US008945066B2

(12) United States Patent
Bochenko et al.

(10) Patent No.: US 8,945,066 B2
(45) Date of Patent: Feb. 3, 2015

(54) MEDICATION INJECTION SITE AND DATA COLLECTION SYSTEM

(71) Applicant: CRISI Medical Systems, Inc.

(72) Inventors: Walter John Bochenko, Encinitas, CA (US); Stephen Michael Prince, La Jolla, CA (US); Shawn Wayne DeKalb, San Diego, CA (US); Winthrop De Childers, San Diego, CA (US)

(73) Assignee: CRISI Medical Systems, Inc., San Diego, CA (US)

( * ) Notice: Subject to any disclaimer, the term of this patent is extended or adjusted under 35 U.S.C. 154(b) by 0 days.

(21) Appl. No.: 13/777,964

(22) Filed: Feb. 26, 2013

(65) Prior Publication Data
US 2013/0204227 A1    Aug. 8, 2013

Related U.S. Application Data

(63) Continuation of application No. 13/777,831, filed on Feb. 26, 2013, which is a continuation-in-part of application No. 12/938,300, filed on Nov. 2, 2010, now Pat. No. 8,385,972, which is a
(Continued)

(51) Int. Cl.
*A61M 3/00* (2006.01)
*G06Q 50/22* (2012.01)
(Continued)

(52) U.S. Cl.
CPC ............... *G06Q 50/22* (2013.01); *A61M 5/31* (2013.01); *A61B 5/117* (2013.01);
(Continued)

(58) Field of Classification Search
CPC ............ G06F 19/3468; G06F 19/3462; G06F 19/3412; G06Q 50/24; A61M 2205/6054; A61M 2205/60; A61M 2025/6063; A61J 2205/60
USPC ............................ 604/65–67, 93.01, 131, 151
See application file for complete search history.

(56) References Cited

U.S. PATENT DOCUMENTS 5,338,157 A    8/1994  Blomquist
5,713,856 A    2/1998  Eggers et al.
(Continued)

FOREIGN PATENT DOCUMENTS

EP    1980974 A2    10/2008

OTHER PUBLICATIONS

Google Scholar Search [Jul. 21, 2014].

*Primary Examiner* — Nicholas Lucchesi
*Assistant Examiner* — Gerald Landry, II
(74) *Attorney, Agent, or Firm* — Mintz Levin Cohn Ferris Glovsky and Popeo, P.C.

(57) ABSTRACT

A medication delivery apparatus for use with a medication container includes a housing, a fluid conduit at least partially extending within the housing and configured to deliver medication within the medication container to a patient, a medication port extending from the housing and configured to be coupled to a fluid outlet of the medication container, the medication port being fluidically coupled to the fluid conduit, and at least one sensor disposed within the housing to generate information characterizing administration of the medication for processing by a remote data collection system. The housing can have a size and shape that enables it to be supported by a first hand of a user while the user administers the medication from the medication container via the medication port using a second hand of the user. Related apparatus, systems, and techniques are also described.

23 Claims, 25 Drawing Sheets

Related U.S. Application Data continuation-in-part of application No. 12/765,707, filed on Apr. 22, 2010, now Pat. No. 8,355,753, which is a continuation-in-part of application No. 12/614,276, filed on Nov. 6, 2009, now Pat. No. 8,394,053.

(60) Provisional application No. 61/370,974, filed on Aug. 5, 2010.

(51) Int. Cl.
| | | |
|---|---|---|
| *A61M 5/31* | (2006.01) | |
| *A61B 5/117* | (2006.01) | |
| *G06F 19/00* | (2011.01) | |
| *A61M 39/02* | (2006.01) | |
| *A61B 5/00* | (2006.01) | |

(52) U.S. Cl.
CPC ....... *G06F 19/3462* (2013.01); *G06F 19/3468* (2013.01); *A61M 39/02* (2013.01); *A61M 2205/6072* (2013.01); *A61M 2205/6063* (2013.01); *A61B 5/0022* (2013.01); *A61M 2205/33* (2013.01); *A61M 2205/3576* (2013.01); *A61M 2205/60* (2013.01); *A61M 2039/0205* (2013.01); *A61M 2205/3561* (2013.01); *A61M 2205/3592* (2013.01); *A61M 2205/6036* (2013.01); *A61M 2205/6054* (2013.01)
USPC ............................................ 604/189; 604/67

(56) References Cited

U.S. PATENT DOCUMENTS

| | | | |
|---|---|---|---|
| 5,781,442 | A | 7/1998 | Engleson et al. |
| 5,920,263 | A | 7/1999 | Huttenhoff et al. |
| 5,941,846 | A | 8/1999 | Duffy et al. |
| 6,039,251 | A | 3/2000 | Holowko et al. |
| 6,270,455 | B1 | 8/2001 | Brown |
| 6,277,099 | B1 | 8/2001 | Strowe et al. |
| 6,471,089 | B2 | 10/2002 | Liff et al. |
| 6,671,563 | B1 | 12/2003 | Engelson et al. |
| 6,685,678 | B2 | 2/2004 | Evans et al. |
| 6,731,989 | B2 | 5/2004 | Engleson et al. |
| 6,851,615 | B2 | 2/2005 | Jones |
| 6,915,170 | B2 | 7/2005 | Engleson et al. |
| 6,993,402 | B2 | 1/2006 | Klass et al. |
| 7,061,831 | B2 | 6/2006 | De La Huerga |
| 7,074,205 | B1 | 7/2006 | Duffy et al. |
| 7,074,209 | B2 | 7/2006 | Evans et al. |
| 7,096,072 | B2 | 8/2006 | Engleson et al. |
| 7,103,419 | B2 | 9/2006 | Engleson et al. |
| 7,107,106 | B2 | 9/2006 | Engleson et al. |
| 7,115,113 | B2 | 10/2006 | Evans et al. |
| 7,117,041 | B2 | 10/2006 | Engleson et al. |
| 7,171,277 | B2 | 1/2007 | Engleson et al. |
| 7,364,067 | B2 | 4/2008 | Steusloff et al. |
| 7,370,797 | B1 | 5/2008 | Sullivan et al. |
| 7,384,410 | B2 | 6/2008 | Eggers et al. |
| 7,483,756 | B2 | 1/2009 | Engleson et al. |
| 7,771,385 | B2 | 8/2010 | Eggers et al. |
| 7,922,073 | B2 | 4/2011 | de la Huerga |
| 7,933,780 | B2 | 4/2011 | De La Huerga |
| 8,240,550 | B2 | 8/2012 | Steusloff et al. |
| 8,303,547 | B2 | 11/2012 | Brown |
| 8,480,834 | B2 | 7/2013 | Rice et al. |
| 8,505,809 | B2 | 8/2013 | Steusloff et al. |
| 8,636,202 | B2 | 1/2014 | Keefe et al. |
| 8,639,521 | B2 | 1/2014 | Eggers et al. |
| 8,639,525 | B2 | 1/2014 | Levine et al. |
| 8,645,154 | B2 | 2/2014 | Eggers et al. |
| 2002/0040208 | A1* | 4/2002 | Flaherty et al. .......... 604/288.01 |
| 2002/0077852 | A1 | 6/2002 | Ford et al. |
| 2003/0135388 | A1 | 7/2003 | Martucci et al. |
| 2006/0122577 | A1* | 6/2006 | Poulsen et al. ............. 604/890.1 |
| 2006/0190302 | A1 | 8/2006 | Eggers et al. |
| 2006/0287887 | A1 | 12/2006 | Hutchinson et al. |
| 2007/0186923 | A1* | 8/2007 | Poutiatine et al. ....... 128/200.14 |
| 2008/0234630 | A1* | 9/2008 | Iddan et al. ..................... 604/48 |
| 2009/0126483 | A1 | 5/2009 | Blendinger et al. |
| 2010/0179417 | A1* | 7/2010 | Russo ........................... 600/424 |
| 2011/0313349 | A1* | 12/2011 | Krulevitch et al. ............. 604/65 |
| 2012/0004542 | A1* | 1/2012 | Nemoto et al. ................ 600/432 |
| 2012/0041355 | A1* | 2/2012 | Edman et al. ................... 604/20 |
| 2013/0105568 | A1 | 5/2013 | Jablonski et al. |
| 2013/0181046 | A1 | 7/2013 | Fedorko et al. |
| 2013/0225945 | A1 | 8/2013 | Prince et al. |
| 2013/0226137 | A1 | 8/2013 | Brown |
| 2013/0327822 | A1 | 12/2013 | Keefe et al. |
| 2014/0039383 | A1* | 2/2014 | Dobbles et al. ................. 604/66 |
| 2014/0060729 | A1 | 3/2014 | Srnka et al. |
| 2014/0142975 | A1 | 5/2014 | Keefe et al. |

* cited by examiner

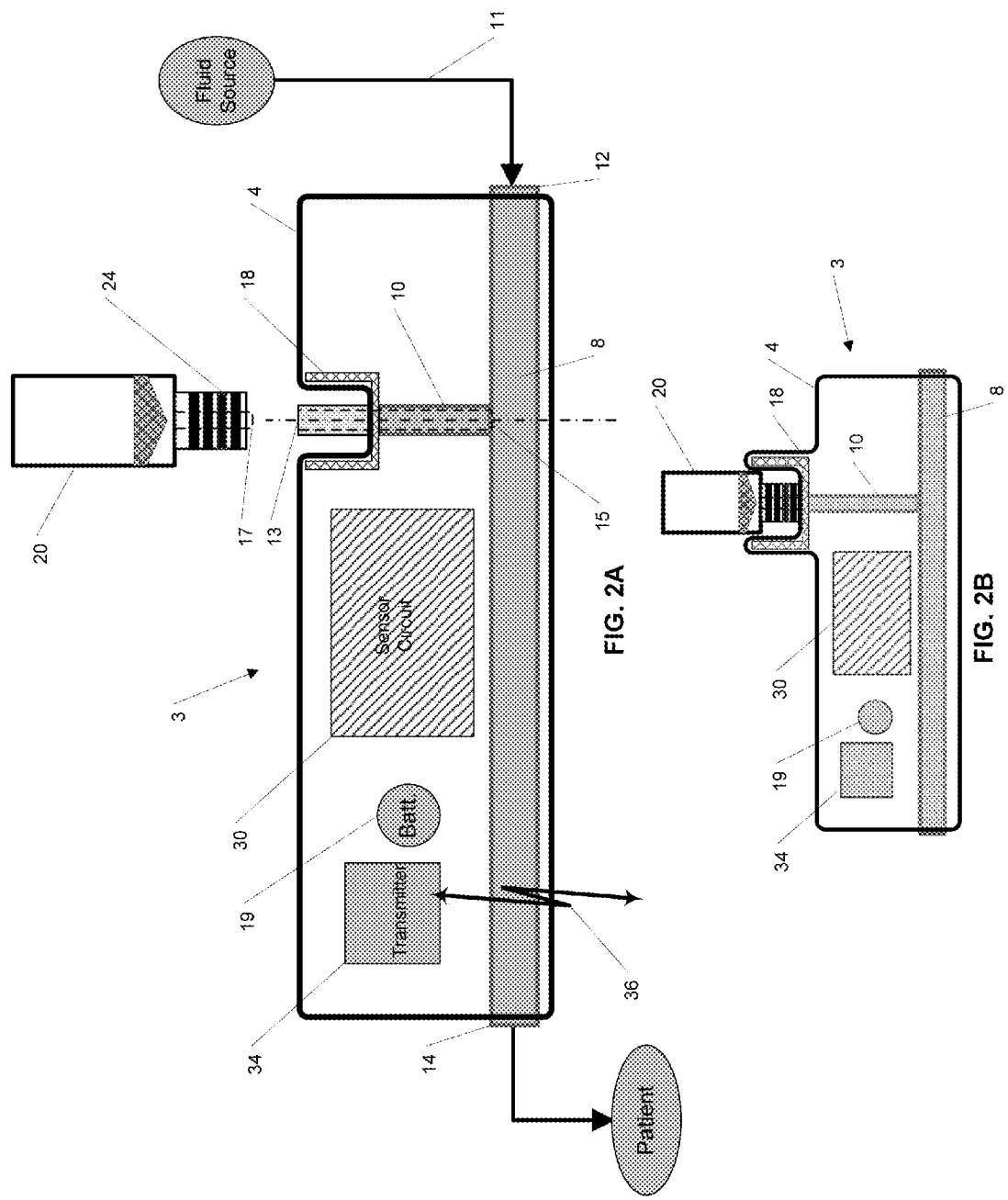

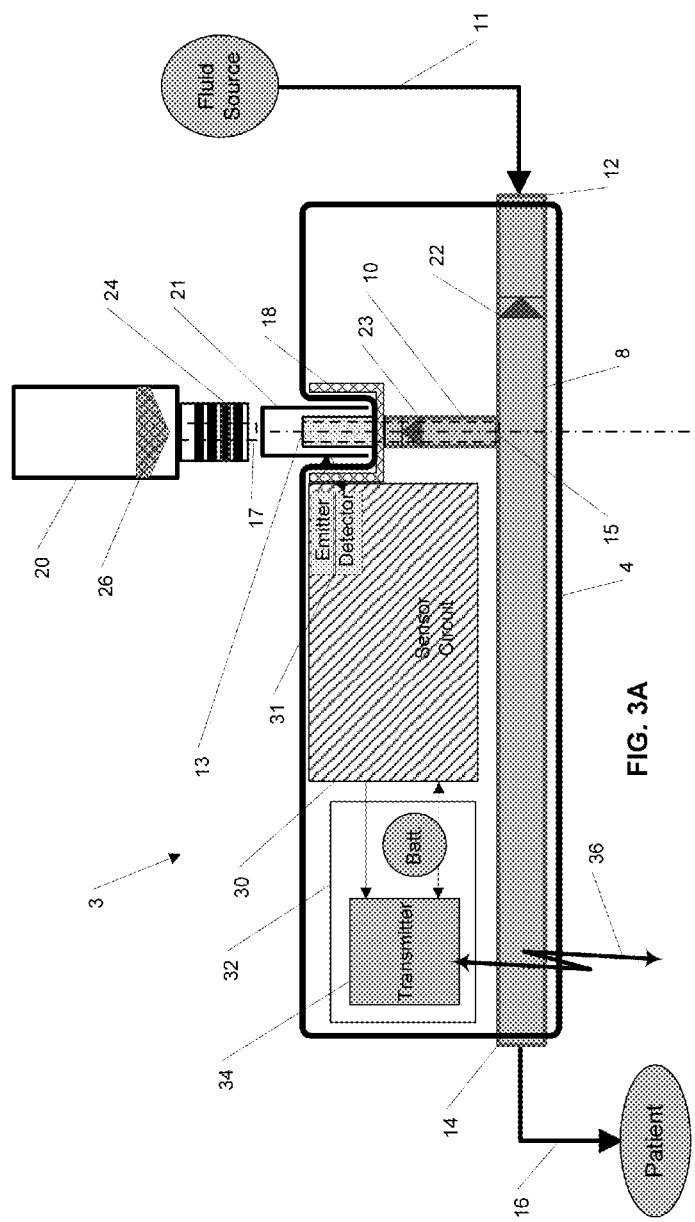
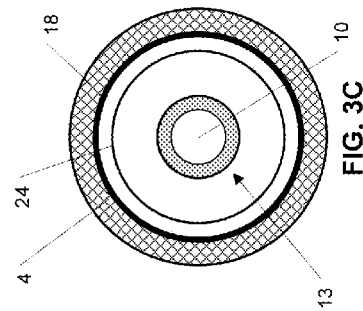
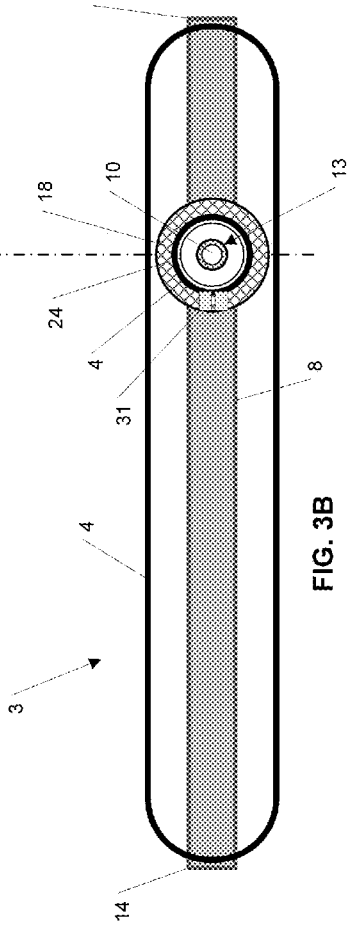

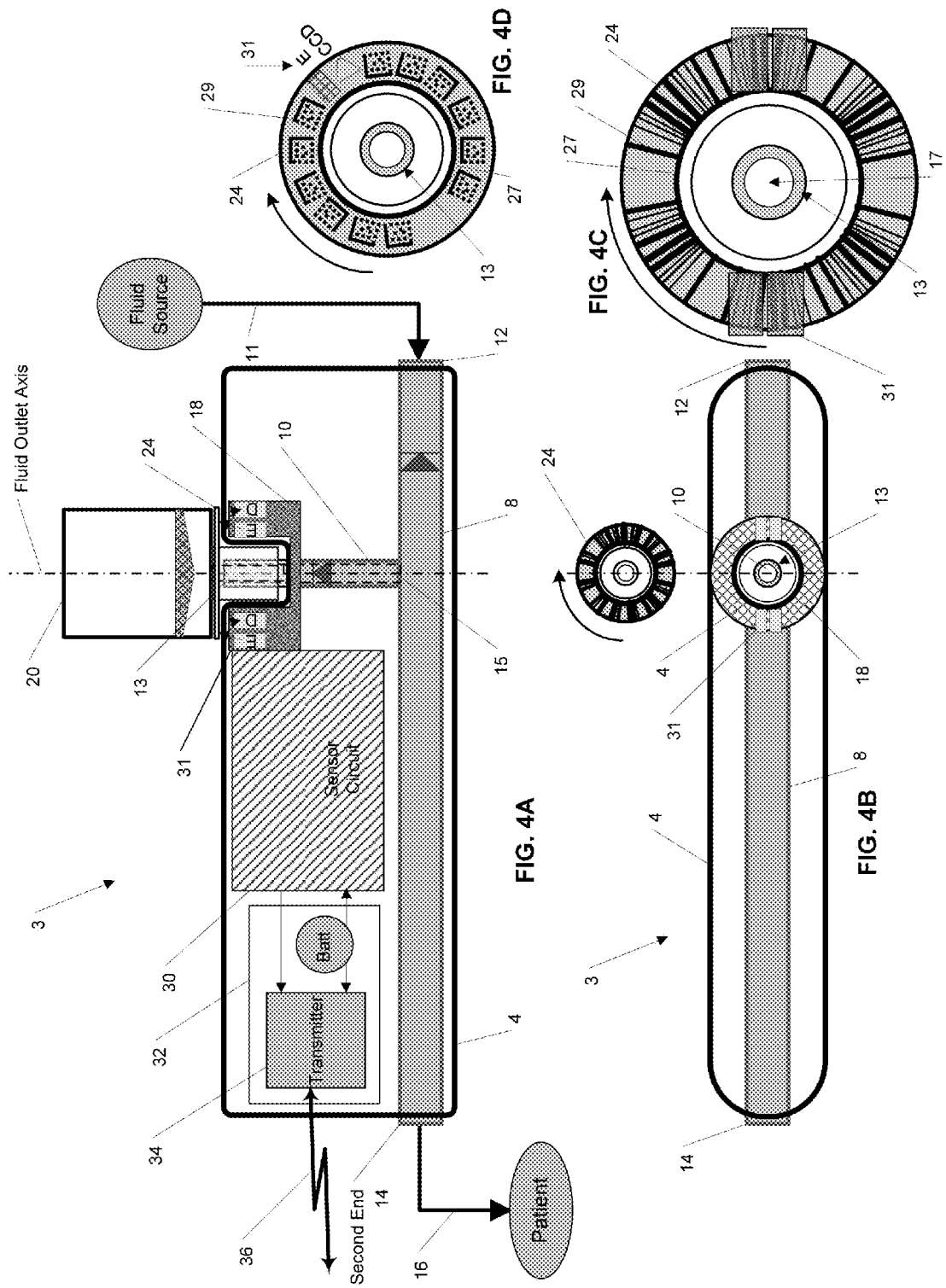

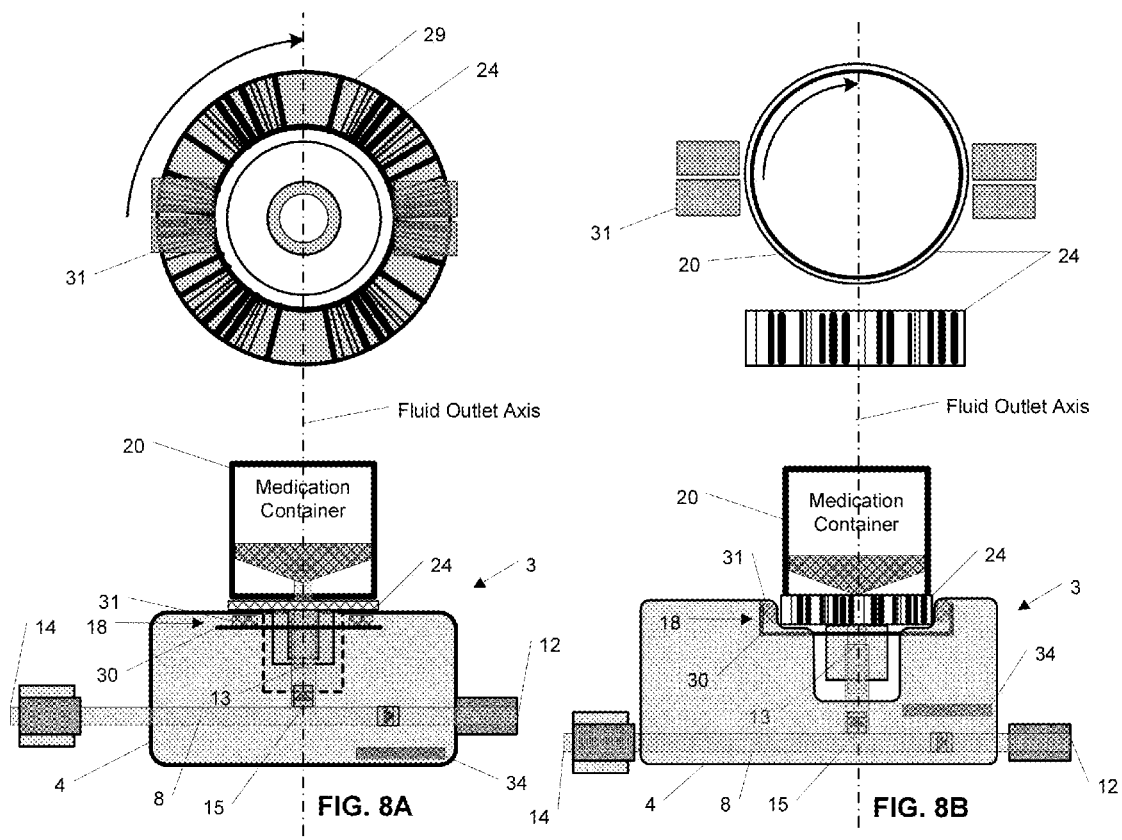
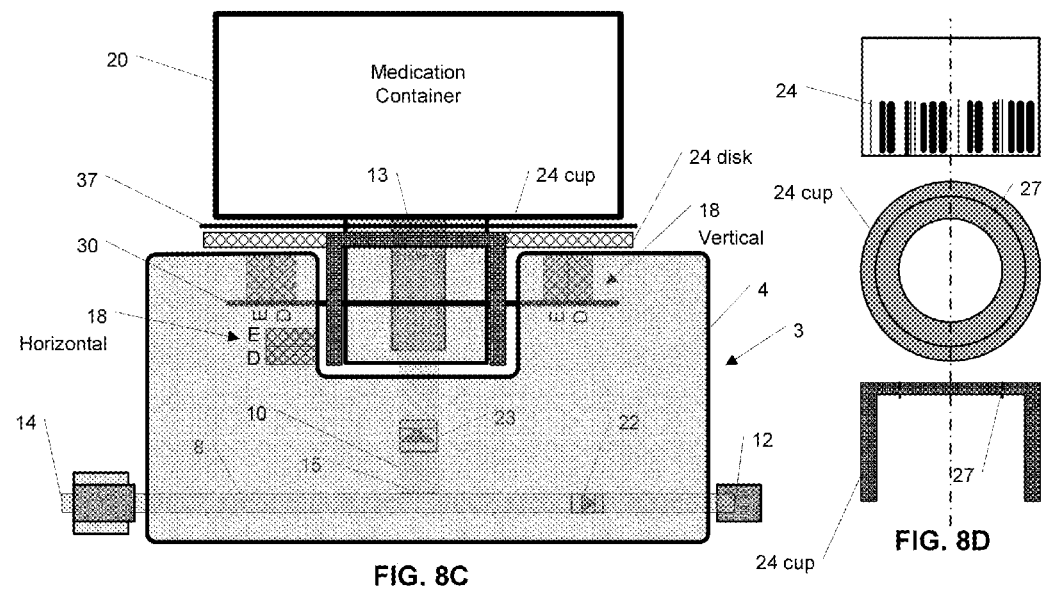
FIG. 8A  FIG. 8B  FIG. 8C  FIG. 8D

9A – Straight thru flow w/Side Port

9B - Right Angle flow w/Side Port

9C - "Y" Site w/Flow-thru Port

Volume = Rate x Time
V = R x T

Discharge Rate = R $R = C_S \times A2/A1 \sqrt{2g \times (p1-p2)}$

Cs = emperical system constant
g = density of fluid

MEDICATION INJECTION SITE AND DATA COLLECTION SYSTEM

RELATED APPLICATIONS

This application is a continuation of U.S. patent application Ser. No. 13/777,831 filed on Feb. 26, 2013, which is a continuation-in-part of U.S. patent application Ser. No. 12/938,300 filed on Nov. 2, 2010, which in turn is a continuation-in-part of U.S. patent application Ser. No. 12/765,707 filed on Apr. 22, 2010, which in turn is a continuation-in-part of U.S. patent application Ser. No. 12/614,276 filed on Nov. 6, 2009; and additionally, priority is also claimed to U.S. Pat. App. Ser. No. 61/370,974 filed on Aug. 5, 2010. Each of the aforementioned patent applications are entitled: "Medication Injection Site and Data Collection System", and are hereby fully incorporated by reference.

FIELD

The subject matter described herein relates to a medication injection site for intelligent delivery of medications into a fluid path for delivery to a patient as well as related data collection and healthcare information systems.

BACKGROUND

Many health care procedures involve medication administrations. The type of medication and timing of administration are important to record in order to provide healthcare providers real-time information on the conduct of the procedure and the completion of a medical record. Some protocols require quick medication administrations with limited time for documentation and record keeping. Others require completion and verification of medication administration manually to ensure proper patient care and accounting for use of medications. To ensure proper safety, all medication administrations require the administering clinician to verify the "5 rights"—right patient, right medication, right dose, right time, and right route, which necessitates the collection, association, and recording of multiple data elements for each drug given. Additionally, medication administration requires careful management of injection sites to maintain patency and infection control.

SUMMARY

In one aspect, a medication delivery apparatus for use with a medication container is provided. The apparatus can include a housing, a fluid conduit at least partially extending within the housing and configured to deliver medication within the medication container to a patient, a medication port extending from the housing and configured to be coupled to a fluid outlet of the medication container, the medication port being fluidically coupled to the fluid conduit, and at least one sensor disposed within the housing to generate information characterizing administration of the medication for processing by a remote data collection system. The housing can have a size and shape that enables it to be supported by a first hand of a user while the user administers the medication from the medication container via the medication port using a second hand of the user.

In another aspect, a medication site is provided that includes a housing, a junction element, a medication port, one or more identification sensors, a transmitter, and a self-contained power source. The junction element can at least partially extend within the housing to form a first fluid channel and a second fluid channel. The first fluid channel extends from a first end to a second end. The first end can be configured to be coupled to a fluid source. The second end of the first fluid channel can be configured to form a fluid outlet of the medication injection site to enable coupling to a parenteral fluid delivery access device (e.g. intravenous, intraosseous, intra-arterial, intramuscular, subcutaneous access device).

The second fluid channel extends from a distal end and terminates at the first fluid channel at an intersection intermediate the first end and the second end. The medication port is fluidically coupled to the distal end of the second fluid channel and is configured to be fluidically coupled to a fluid outlet of a medication container. The identification sensor is disposed within the housing to generate information indicative of contents of the medication container when the fluid outlet of the medication container is fluidically coupled to the medication port. The transmitter is disposed within the housing and in communication with the identification sensor to wirelessly transmit the information generated by the identification sensor to a remote data collection system. The term transmitter in this context can refer to a transmitter only or a transceiver, a combined transmitter-receiver (unless otherwise specified). The self-contained power source is disposed within the housing and it powers components within the medication injection site such as the identification sensor and the transmitter. In some implementations, the housing has a shape and size enabling it to be held by a first hand of a user while the user administers medication from the medication container via the medication port using his or her second hand.

In a further aspect, a medication injection site is provided that includes a housing separated from and does not include the first fluid channel or a junction element. In this implementation, the second fluid channel becomes the only fluid channel. The housing includes a medication port, an identification sensor, a transmitter and a self-contained power source. The medication port is fluidically coupled to the distal end of the second fluid channel and can be configured to be fluidically coupled to a fluid outlet of a medication container. The proximal end of the second channel can be configured to form a fluid outlet of the medication injection site to enable direct coupling to a parenteral fluid delivery access device (e.g. intravenous, intraosseous, intra-arterial, intramuscular, subcutaneous access device) with little or no intermediate tubing (e.g., 10 cm or less, etc.). Examples of direct coupling can include, but are not limited to, connection to a "Y" site of a tubing set, a patient's catheter, an intraosseous access device or a needle for direct fluid injection.

A largest dimension of the housing can, in some implementations, be less than or equal to 10 centimeters. In addition or in the alternative, a weight of the system can be less than or equal to 500 grams, and in some implementations, less than or equal to 250 grams, and in other implementations less than or equal 100 grams. In still further implementations, the weight can be ultra-lightweight and be less than 50 grams.

The first end of the first fluid channel can be fluidically coupled to tubing extending to a fluid source. The fluid source can be suspended (e.g., IV drip bag, etc.) and fluid contained therein can be gravity fed via the tubing into the first channel. With such a variation, the housing can be suspended below the fluid source and supported by the tubing during use. The second end of the first fluid channel can be fluidically coupled to a patient. In other variations the housing can be located downstream more closely associated with the patient's catheter.

A self-contained fluid delivery sensor can be disposed within the housing and in communication with the transmitter to characterize fluid flow through one or more of the first fluid channel and the second fluid channel. With such arrangements, the transmitter can wirelessly transmit data characterizing fluid delivery to the remote data collection system. The fluid delivery sensor can measure fluid flow, volume, medication or fluid type composition and/or pressure in the first fluid channel. Alternatively or in addition, the fluid delivery sensor measures fluid flow, volume, medication or fluid type composition and/or pressure in the second fluid channel. The fluid delivery sensor can either be a pressure sensor, a differential pressure sensor, an optical sensor, an ultrasonic sensor, a chemical sensor, a conductivity sensor, a medication composition sensor, a displacement sensor or a fluid flow sensor or a combination of these or other fluid delivery sensors.

In some implementations, a medication composition sensor can be utilized in order to verify and/or determine the contents of the medication container. The medication composition sensor can automatically determine the composition of the medication injected from the medication container. This can be a sensor or plurality of sensors that determine the fluid type being injected. This can be compared to the medication type indicated by the medication ID Code, if present. The sensor can be any one or more of a pH detector, a viscosity indicator, an optical density indicator, a chemical indicator, a drug molecule indicator, a drug sensor, a spectrophotometer, an HPLC detector, a UV detector, a fluid density sensor, a specific gravity fluid sensor, etc.

The junction element can contain a diaphragm portion along one or more of the first fluid channel and the second fluid channel and the fluid delivery sensor can be positioned adjacent to the diaphragm.

The remote data collection system can calculate volume of fluid delivered via the medication port based on the wireless transmitted data characterizing fluid delivery. Alternately, or in addition, the volume of fluid delivered can be calculated locally within the medication port housing and such volume data can be transmitted wirelessly to the remote data collection system.

A self-contained power source can be disposed within the housing to power one or more of the identification sensor, the fluid delivery sensor, and the transmitter.

An intersection of the first fluid channel and the second fluid channel can form a substantially T-shaped junction. In other variations, an intersection of the first fluid channel and the second fluid channel can form a substantially Y-shaped junction.

The medication port can define a cavity extending inwardly from an outer surface of the housing such that the fluid outlet of the medication container is substantially enveloped within the housing and does not extend beyond the outer surface when such fluid outlet is mechanically coupled to the port. The medication port can be a needleless injection port or a one-way port valve.

The medication container can bear an information source characterizing the medication container and/or its contents. The information source can be, for example, mechanically encoded information, magnetically encoded information, and radio frequency readable information. The information source can also or alternatively comprise optically encoded information and the identification sensor can comprise an optical emitter and an optical detector to read the optically encoded information. The identification sensor can include an optical emitter LED to illuminate the information source and an optical detector such as a camera (charge coupled device—CCD). The identification sensor can read information from the information source as a result of relative motion of the fluid outlet of the medication container relative to the medication port. The identification sensor can read information from the information source in response to mechanically coupling the fluid outlet to the medication port.

The medication container can be a needle-less syringe, and the fluid outlet can be a tip of the syringe. The medication container can be a vial and the fluid outlet can be the stopper at the vial closure. The medication container can be a pre-mixed solution provided in a bag, and the fluid outlet can be a luer fitting connector or an IV set spikeable port. The medication container can be a small disposable, rigid, semi-rigid or flexible envelope that contains medication for administration to a patient and the fluid outlet can be an integral luer fitting on the container, at the end of tubing attached to the container or part of a fluid transfer device used with medication vials. The medication container can be a fluid delivery tubing set and the fluid outlet can be an integral luer fitting at the end of tubing attached to the container.

The junction element can be a unitary injection molded fitting.

Medication can be intermittently delivered through the medication port such that it is continuously or substantially continuously delivered to the first fluid channel via the first end of the first fluid channel. Alternately, medication can be intermittently delivered through the medication port such that it is only delivered to the second fluid channel.

A first check valve can be disposed within the first fluid channel intermediate the intersection and the first end of the first fluid channel to prevent fluid delivered into the medication port from exiting the first fluid channel at the first end. A second check valve can be disposed within the secondary fluid channel to prevent fluid entering the first fluid channel at the first end from exiting the secondary fluid channel at the distal end. The second check valve can be the needleless injection port or a one-way port valve.

The housing can comprise a plurality of sections, and one or more of the first fluid channel and the second channel can be formed when at least two of the sections are assembled. At least two of the sections of the housing can be injection molded and one or more of the first fluid channel and the second fluid channel can be formed by one or more injection molded sections.

In one implementation, the medication injection site can be separated into two sub-housings, a reusable sub-housing, a disposable sub-housing that are coupled to each other via a connection interface. The reusable sub-housing can be used by one or more patients while the disposable sub-housing is intended to only be used by a single patient (i.e., the components contained within the disposable sub-housing provide a sterile fluid passageway which are separate from the components within the reusable sub-housing ensuring patient safety). The reusable sub-housing can contain elements of the medication injection site that are not part the first fluid channel or the second fluid channel (e.g., one or more of the identification sensor(s), the fluid delivery sensor, the transmitter, a processor, a memory, etc.). The disposable sub-housing can contain one or both of the first fluid channel and the second fluid channel. The power source can be positioned in either sub-housing.

A removable sterility cap can be affixed to the medication port. Removal of the sterility cap can initiate communications between the transmitter and the remote data collection system.

A self-contained power source (e.g., battery, battery array, etc.) can be disposed within the housing powering one or more of the identification sensors, the fluid delivery sensor, and the transmitter. Removal of the sterility cap affixed to the medication port can initiate provision of electricity by the power source to the identification sensors and the transmitter.

The shape and size of the housing can enable positioning of the housing on the arm or leg of a patient adjacent to an injection site on the patient, positioned on a "Y" site of fluid delivery tubing set, connected directly to a patient catheter or attached to a needle for direct injection. The shape and size of the housing can enable positioning of the housing on a patient at or near a peripheral venous access site, a central venous line, a subcutaneous access site, an intra-muscular access site, or an intraosseous access device.

The medication port, can in some variations, be disposed wholly or at least substantially wholly within the housing. The medication port can additionally or alternatively be integrated into the junction element.

A memory element can be disposed within the housing that can store information obtained from the identification sensors and/or the fluid delivery sensor. A timing element can be coupled to the memory element to enable recordation of events corresponding to what medication is administered, the time of medication administration, what volume of medication was administered, the duration of medication administration, identification sensor information from a second information source and the time of wireless transmission of information generated by the identification sensors. The remote data collection system can wirelessly request the transmitter to send information stored in the memory element obtained from the sensors. In addition, the remote data collection system can comprise a timing element to assign clock times to each data record based on absolute time and duration between recorded transmissions.

The system can include an identifier (e.g., serial number or alphanumeric identifier, bar code label, etc.) to uniquely identify wireless transmissions from the transmitter. The identifier can be encapsulated in some or all of the wireless transmissions, or it can be manually accessed or scanned by a practitioner.

The medication injection site can be enveloped in a sterile pouch (i.e., enclosure, etc.). The medication injection site can be part of a kit that also contains instructions for use.

In a first interrelated aspect, a medication injection site includes a housing, a junction element, a medication port, one or more identification sensors, a transmitter, and a self-contained power source. The junction element at least partially extends within the housing forming a first fluid channel and a second fluid channel. The first fluid channel extends from a first end to a second end. The second fluid channel extends from a distal end and terminates at the first fluid channel at an intersection intermediate the first end and the second end. The medication port is fluidically coupled to the distal end of the second fluid channel and is can be configured to be fluidically coupled to a fluid outlet of a medication container. One identification sensor can be disposed adjacent to the second fluid channel to generate information indicative of contents of the medication container when the fluid outlet of the medication container is fluidically coupled to the medication port. A second identification sensor can be disposed within the housing to generate information complementary to the medication container information (e.g., information about the patient, about the medication procedure, the medication and/or its preparation, the caregiver administering the medication, etc.). The transmitter is disposed within the housing and in communication with the identification sensors to wirelessly transmit the information generated by the identification sensors to a remote data collection system. A self-contained power source is disposed within the housing powering the identification sensors and the transmitter.

Activation of the second identification sensor can be manual (user manipulation, etc.) or automated (apparatus is activated remotely, etc.). Activation can be through mechanical, electronic, optical, magnetic or remote communication means.

A self-contained fluid delivery sensor can be disposed within the housing and in communication with the transmitter to characterize fluid flow through one or more of the first fluid channel and the second fluid channel. With such a variation, the transmitter further can wirelessly transmit data characterizing fluid delivery to the remote data collection system.

In yet another interrelated aspect, a medication injection site includes a housing, a medication port extending from an outer surface of the housing, an identification sensor disposed within the housing to generate information indicative of contents of the medication container when the fluid outlet of the medication container is fluidically coupled to the medication port, an identification sensor disposed within the housing to generate information complementary to the contents of the medication container when the sensor is proximal to the complementary information source, a transmitter disposed within the housing and in communication with the identification sensors to wirelessly transmit the information generated by the identification sensors to a remote data collection system. The housing has a shape and size enabling it to be held by a first hand of a user while the user administers medication from the medication container via the medication port using his or her second hand.

In a further interrelated aspect, an apparatus to identify contents of a medication container is provided. Such a medication container includes a barrel portion, a fluid outlet tip, and a tapered portion intermediate the barrel portion and the fluid outlet tip. The apparatus includes an identification member having an opening larger than a diameter of the fluid outlet tip and smaller than or equal to the diameter of the barrel portion. In other variations the identification member can be slightly larger in diameter than the barrel portion. The identification member can contain optical, magnetic, and/or mechanically encoded information. The information can be indicative of one or more of the contents of the medication container, the volume of fluid within the medication container, and the expiration date of the contents of the medication container. Additionally, information on the identification member can include a unique identifier (such as a serial number, random ID identifier {alpha-numeric sequence, hexadecimal code with-or-without a prefix, suffix, code base subscript number} or other unique information data, prefix, suffix, symbol or color, etc.). This information can be used to identify the container and provide for tracking it through the medication usage cycle. The information can be patient specific or patient neutral.

The information can be readable by an identification sensor when the identification member is located around the fluid outlet tip and the apparatus is coupled to or adjacent to a fluid delivery system to deliver contents of the medication container.

In a further interrelated aspect, an apparatus (e.g., a complementary data sensor, etc.) to identify information complementary to the medication container can be provided (either integrated into the medication injection site or used in conjunction with same). The apparatus can include a second identification member and identification sensor. The second identification member can contain optical (1 dimensional barcode, 2 dimensional barcode, symbol, image or picture), magnetic (magnetic strip on an identification card/badge/ID tag), a Near Field Communication (NFC) tag, RFID, and/or mechanically encoded information. The information can be indicative of one or more of the following: a patient (patient ID, weight, height, sex, age, pre-existing medical conditions, current medical state, Broselow color); a patient sample (sample ID, blood sample, urine sample, tissue sample, stool sample, other body fluid sample, etc.); a medical device (device ID, IV pump, EKG monitor, defibrillator, pulse oximeter, blood pressure monitor, etc.); a caregiver (picture, ID, name, affiliation, etc); a pharmacy record (prescription, patient ID, medication formulation, preparation date, expiration date, administration instructions and or precautions, pharmacy ID, preparer ID, etc.).

This information can be used to associate treatment information with a medication injection and with its use on a particular patient. The information can be readable by an identification sensor when the identification member is located proximal to the identification sensor or is coupled to or adjacent to the apparatus.

In a further aspect, a medication injection site is provided that includes a housing separated from the first fluid channel. In this variation, the second fluid channel becomes the only fluid channel. The medication port is fluidically coupled to the distal end of the second fluid channel and can be configured to be fluidically coupled to a fluid outlet of a medication container. The proximal end of the second channel can be configured to form a fluid outlet of the medication injection site to enable direct coupling to a parenteral fluid delivery access device. An identification sensor is disposed adjacent to the second fluid channel to generate information indicative of contents of the medication container when the fluid outlet of the medication container is fluidically coupled to the medication port. A second identification sensor (sometimes referred to as a complementary data sensor, etc.) can be disposed within the housing to generate information complementary to the contents of the medication container when the sensor is proximal to the complementary information source. The transmitter is disposed within the housing and in communication with the identification sensors to wirelessly transmit the information generated by the identification sensors to a remote data collection system. Additionally, a fluid delivery sensor can be disposed within the housing and in communication with the transmitter to wirelessly transmit the information generated by a fluid flow/volume sensor to a remote data collection system. A self-contained power source can be disposed within the housing powering the identification sensors, fluid delivery sensor and the transmitter.

In yet another aspect, a housing can include a reusable sub-housing and a disposable sub-housing. The reusable sub-housing can be operatively coupled to the disposable sub-housing. In addition, the reusable sub-housing is intended for use by a plurality of patients and the disposable sub-housing is intended for use by a single patient. Such an arrangement can also include a medication port configured to be fluidically coupled to a fluid outlet of a medication container, an identification sensor disposed within the housing to generate information indicative of contents of the medication container when the fluid outlet of the medication container is fluidically coupled to the medication port, a transmitter disposed within the housing and in communication with the identification sensor to wirelessly transmit the information generated by the identification sensor to a remote data collection system, and a power source disposed within the housing powering the identification sensors and the transmitter.

In one implementation, the medication port is within the disposable sub-housing and one or more of the identification sensors, the transmitter, and the power source are in the reusable sub-housing.

The identification member can be disposed radially about a central fluid outlet axis of the fluid outlet tip enabling detection of the information when the medication container is rotated about the central fluid outlet axis.

The information can be disposed linearly enabling detection of the information when the medication container is joined with a fluid pathway along a central fluid outlet axis of the medication container. The information can be selected from a group comprising: optically encoded information, magnetically encoded information, radio frequency detectable information, and mechanically detectable information.

The medication container can be a first medication container and the identification member can be releasably secured to the medication container to allow it to be removed for placement on a second medication container. The identification member can bear an attachment element allowing it to be removed from the first medication container and affixed to the second medication container. Transfer of the identification member from the first medication container to the second medication container can be completed during the process of transferring the medication from the first medication container to the second medication container.

The identification member can be a label or other element adhered to, printed on, and/or etched onto the medication container. The identification member can be integral to the medication container. The identification member can be a ring shaped member configured to fit around the fluid outlet tip. The identification member can be a disk or cup shaped member configured to fit over the fluid outlet tip.

In another aspect, a system can include a housing, a medication port, a transmitter, and a power source. The medication port is configured to be fluidically coupled to a fluid outlet of a medication container. The identification sensor generates information indicative of contents of the medication container when the fluid outlet of the medication container is fluidically coupled to the medication port. The transmitter is in communication with the identification sensor to wirelessly transmit the information generated by the identification sensor to a remote data collection system. The remote data collection system can be coupled to or integral with a secondary medical device. The power source can power the identification sensor and the transmitter.

The secondary medical device can be, for example, a physiological sensor, a defibrillator, an infusion pump, a ventilator, an anesthesia machine.

Example physiological sensors include an EKG monitor, an EEG monitor, a blood pressure monitor, an ETCO2 monitor, and/or a pulse oximeter. The remote data collection system can also comprise a bar code medication administration (BCMA) system.

The data collection system can receive information from one or more medication injection sites and/or one or more secondary medical devices. The data collection system can be coupled to or form part of a cellular phone or other mobile computing system (e.g., tablet computer, IPAD, etc.). The data collection system can provide collected data to other systems (medical information systems, emergency medical services (EMS) information systems, hospital information systems, remote monitoring systems, event management systems, home health care monitoring systems, medication waste disposal management systems, telemedicine systems, etc.) and or receive information from other systems (hospital information systems, remote systems, event management systems, home health care monitoring systems, medication waste disposal management systems, telemedicine systems, etc.). The data collection system can include a set of rules with alerts and alarms to provide healthcare providers with information regarding the medications injected, to be injected or which need to be disposed/wasted.

Still further, in some implementations the housing can comprise at least one fluid characterization sensor. Such at least one fluid characterization sensor can be used to characterize the contents of the medication container and/or administration of the contents of the medication container. The at least one fluid characterization sensor can comprise, for example, an identification sensor and/or a fluid characterization sensor.

In yet a further aspect, a method is provided in which information is received (e.g., by at least one data processor, etc.) from a medication delivery apparatus as described herein that characterizes administration of medication to a patient. Thereafter, the information is associated (e.g., by at least one data processor, etc.) with data specifying at least one medication and/or a volume of medication. Once this association has been performed, the associated data is promoted (e.g., display, store, transport, etc.).

In a further interrelated aspect, a system includes a housing, a medication port, a first identification sensor, a second sensor (which may be a second identification sensor), and a transmitter. The medication port extends from an external face of the housing and is configured to be fluidically and directly coupled to a fluid outlet of a manually injectable medication container comprising medication for administration to a patient. The first identification sensor is disposed within the housing and generates identification information indicative of contents of the medication container when the fluid outlet of the medication container is fluidically coupled or is being fluidically coupled to the medication port. The second sensor is disposed within the housing and detects information on a source other than the medication container that is associated with the administration of the contents of the medication container. The transmitter is disposed within the housing and is in communication with the first identification sensor and the second sensor to wirelessly transmit the information generated by the first identification sensor and the second sensor to a remote data collection system.

One or more of the first identification sensor and the second sensor can include a near field communication (NFC) sensor or a proximity sensor.

The second sensor can further detect information on the medication container that is associated with the administration of the contents of the medication container.

The information detected by the first identification sensor and/or the second sensor can comprise one or more of: a one dimensional barcode, a two dimensional barcode, symbolic information, an image, magnetic media, a near field communication (NFC) tag, biometric data, RFID encoded information.

The information detected by the first identification sensor and/or second sensor can characterize one or more of the patient, demographics associated with the patient, a medical record for the patient, a picture of the patient, a video associated with the patient, a biometric patient identifier (ID), a medical record number, physical characteristics of the patient, allergies of the patient, contraindications, and BROSELOW color.

The information detected by the second sensor can characterize one or more of a patient sample such as a blood sample, a urine sample, a tissue sample, a stool sample, and the like.

The information detected by the second sensor can characterize a medical device such as an intravenous (IV) pump, an EKG monitor, a defibrillator, a pulse oximeter, and a blood pressure monitor.

The information detected by the second sensor can characterize fluids, medications, and food provided to the patient.

The information detected by the second sensor can characterize bodily waste of the patient.

The information detected by the second sensor can characterizes a diagnostic test or treatment result for the patient such as lab values, radiological images, radiological reports, vital sign trends, EKG strip, and clinical reports.

The information detected by the second sensor can characterize a caregiver associated with the patient. The information can characterizing the caregiver associated with the patient can be, for example, a picture of the caregiver, a video of the caregiver, an identification code associated with the caregiver, a password associated with the caregiver, an identification of the caregiver, a name of the caregiver, an affiliation of the caregiver, a responsible clinician associated with the caregiver, a decision-making authority associated with the caregiver.

The information detected by the second sensor can characterize one or more of a person accompanying the patient, a relationship of the person to patient, a companion, a picture of the person, a fingerprint of the person, an affiliation of the patient, a religion of the patient, contact information for the patient, breast milk information associated with the patient, organ donation information for the patient, medical directives associated with the patient, and caregiving instructions associated with the patient.

The information detected by the second sensor can characterize a pharmacy record such as prescription number, patient identifier, formulation, expiration date, administration instructions, precautions instructions, contraindications, medication reconciliation information, pharmacy identifier, and preparer identifier.

The information detected by the second sensor can characterize a physician's order such as medication administrations orders, lab orders, diagnostic testing orders, radiological orders, treatment orders, and therapy orders.

The information detected by the second sensor can characterize an environmental factor associated with the patient such as a room number for the patient, a temperature of the room for the patient, a time, a care transition status, a time of admission of the patient, and a time of last bed sheet change for the patient.

The information detected by the second sensor can characterize one or more of: medication type, medication concentration, medication expiration date, medication NDC, and RxNorm code.

The medication container can be one or more of syringes, vials, fluid bags, ampoules, blood bags, IV tubing sets, medication patches, and auto-injection devices.

The source detected by the second sensor can be one or more of a patient wrist band, an oral solid package, a patient sample container, and a medical device.

The remote data collection system can form part of a barcode medication administration (BCMA) system.

In a further aspect, a system can include a housing, a medication port, a first sensor, a second sensor, and a transmitter. The medication port can extend from an external face of the housing and is configured to be fluidically and directly coupled to a fluid outlet of one of a plurality of manually injectable medication containers. The manually injectable medication containers can have identification information on one or more of a first portion and a second portion and comprising medication for administration to a patient. The first sensor can be disposed within the housing to generate data derived from the identification information on a first portion of a medication container coupled to the medication port (if the medication container has information on the first portion). The second sensor can be disposed within the housing to generate data derived from the identification information on a second portion of a medication container coupled to the medication port (if the medication container has information on the second portion). The transmitter can be disposed within the housing and can be communication with the first sensor and the second sensor to wirelessly transmit data generated by the first sensor and the second sensor to a remote data collection system. In some variations, the first sensor can generate the data when the fluid outlet of the medication container is fluidically coupled or is being fluidically coupled to the medication port.

In a further interrelated aspect, an apparatus includes a housing, a fluid port, an identification sensor, and a transmitter. The fluid port can extend from an outer surface of the housing and is configured to be coupled to a fluid outlet of a fluid container (that can contain a variety of fluids including, for example, medication). The identification sensor can be disposed within the housing to generate information indicative of contents of the fluid container when the fluid outlet of the medication container is fluidically coupled to the fluid port. The transmitter can be disposed within the housing and can be in communication with the identification sensor to wirelessly transmit the information generated by the identification sensor to a remote data collection system. In some variations, the housing can have a shape and size enabling it to be held by a first hand of a user while the user administers fluid from the fluid container via the fluid port using his or her second hand.

In one variation, a method can be implemented by an apparatus that includes a housing, a medication port extending from an external face of the housing configured to be fluidically and directly coupled to a fluid outlet of a manually injectable medication container comprising medication for administration to a patient, a first identification sensor disposed within the housing to generate identification information indicative of contents of the medication container when the fluid outlet of the medication container is fluidically coupled or is being fluidically coupled to the medication port, a second sensor disposed within the housing to detect information on a source other than the medication container that can be associated with the administration of the contents of the medication container, and a transmitter disposed within the housing and in communication with the first identification sensor and the second sensor to wirelessly transmit the information generated by the first identification sensor and the second sensor to a remote data collection system. The method can include generating data by the first identification sensor indicative of contents of the medication container when the fluid outlet of the medication container is fluidically coupled or is being fluidically coupled to the medication port, generating data by the second sensor associated with the administration of the contents of the medication container, and transmitting the data generated by the first identification sensor and the second sensor to the remote data collection system.

In a further aspect, a method can be provided that is implemented by one or more data processors that includes receiving, by at least one data processor, information from a medication delivery apparatus characterizing administration of medication to a patient, associating, by at least one data processor, the information with data specifying at least one medication and/or a volume of medication, and promoting the associated data. The medication delivery apparatus can include a housing, a medication port extending from an external face of the housing configured to be fluidically and directly coupled to a fluid outlet of a manually injectable medication container comprising medication for administration to a patient, a first identification sensor disposed within the housing to generate identification information indicative of contents of the medication container when the fluid outlet of the medication container is fluidically coupled or is being fluidically coupled to the medication port, a second sensor disposed within the housing to detect information on a source other than the medication container that is associated with the administration of the contents of the medication container, and a transmitter disposed within the housing and in communication with the first identification sensor and the second sensor to wirelessly transmit the information generated by the first identification sensor and the second sensor to a remote data collection system.

In a further aspect, a system can include a housing, a medication port, a first identification sensor, a second identification sensor, and a transmitter. The medication port can extend from an external face of the housing and can be configured to be fluidically and directly coupled to a fluid outlet of a manually administrable medication container comprising medication for administration to a patient. The first identification sensor can be disposed within the housing to generate identification information indicative of the contents of a medication container when the fluid outlet of the medication container is fluidically coupled or is being fluidically coupled to the medication port. The second identification sensor can be disposed within the housing to detect information indicative of the contents of a medication container intended for administration to a patient when the medication container is in contact with or proximate to the sensor. The transmitter can be disposed within the housing and can be in communication with the first identification sensor and the second identification sensor to wirelessly transmit the information generated by the first identification sensor or the second identification sensor to a remote data collection system.

The first identification sensor or the second identification sensor can generate information indicative of the contents of a fluid medication to be administered to the patient through the medication port.

The second identification sensor can generate information indicative of the contents of a medication container to be administered to the patient through a route other than the medication port.

The medication can be an IV fluid, a subcutaneous fluid, an intramuscular fluid, an oral solid, an oral liquid, a topical preparation, a transdermal patch, or a suppository.

In still a further interrelated aspect, a medication delivery apparatus for use with a medication source is provided that includes a housing, a fluid conduit, a medication port, and at least one first sensor. The fluid conduit can at least partially extend from the housing and can be configured to deliver medication from the medication source to a patient via a parenteral fluid administration pathway. The medication port can extend from an external surface of the housing and can be configured to be coupled to a tubing set coupled to the medication source. In addition, the medication port can be fluidically and directly coupled to the fluid conduit. The at least one first sensor can be disposed within the housing to generate information characterizing administration of the medication for processing by a remote data collection system.

The medication delivery apparatus can include at least one second sensor disposed within the housing to generate complementary information for processing by the remote data collection system. The complementary information can comprise encoded information. The remote data collection system can associate the information generated by the at least one sensor and/or the complementary information generated by the at least one second sensor with one or more of: medication information, patient identification, patient weight, patient sex, patient age, patient BROSELOW color, pre-existing and/or current patient medical conditions, patient sample, medical device being used by the patient, caregiver name, caregiver photograph, caregiver ID, caregiver employer, a pharmacy record, pharmacy administration instructions, physicians orders.

Tubing between the fluid conduit and a parenteral access device can, for example, be 10 cm or less.

The medication delivery apparatus can include a transmitter within the housing to transmit information generated by the at least one sensor to the remote data collection system; and a self-contained power source within the housing powering the at least one first sensor and the transmitter. The remote data collection system can receive information wirelessly from the transmitter.

The housing comprises a reusable sub-housing and a disposable sub-housing, the disposable sub-housing being used by a single patient and including at least the fluid conduit and the medication port, the reusable sub-housing being used by a plurality of patients and including the at least one first sensor. The re-usable sub-housing can be operatively coupled to the disposable sub-housing by a connection interface including one or more of an electrical contact, an RF coupling, an optical coupling, a hydraulic coupling, a mechanical coupling, and a magnetic coupling.

The fluid conduit can include a first fluid channel and a second fluid channel with the first fluid channel extending from a first end to a second end and the second fluid channel extending from a distal end and terminating at the first fluid channel at an intersection intermediate the first end and the second end.

The medication delivery apparatus can be integral to and/or configured to be suspended below a fluid source.

The at least one first sensor can include an identification sensor and the tubing set includes an information source such that the identification sensor reads the information from the information source. The information source can be disposed proximate to a fitting of the tubing set. The information source can be disposed upon a cylindrical or annular surface that is concentric to the fluid outlet of the tubing set and the sensor can generate the information characterizing administration of the medication when the tubing set is coupled and/or being coupled to the medication port.

The at least one first sensor can include a fluid flow sensor and the information can include information indicative of an amount of fluid delivered from the medication source to the patient.

The at least one first sensor can include a medication composition type sensor such that the information includes information characterizing the composition of the medication.

The remote data collection system can receive, transmit, integrate and/or report information from and/or to a medical information source selected from a group comprising: a medical device, and a medical information system.

The remote data collection system can provide real-time information to a user including, for example, medication information, medical data specific to a patient, procedural instructions and/or protocols for patient treatment.

The remote data collection system can provide a rule set defining conditions to alert and/or guide a caregiver using the apparatus.

A memory element can be disposed within the housing for storing information generated by the at least one first sensor.

An indicator element can be disposed within the housing for indicating the operational state of the medication delivery apparatus and/or illuminating the medication port providing user information.

The at least one first sensor can be one or more of a flow volume sensor, a flow rate measurement sensor, a composition sensor, a pressure sensor, an air in line sensor, and a temperature sensor.

The medication delivery apparatus can be included in a kit comprising a sterile pouch. The medication delivery apparatus can be provided within the pouch in a sterile condition.

In another variation, a medication delivery apparatus for use with a medication source can include a housing, a fluid conduit, a medication port, at least one sensor, a transmitter, and a self-contained power source. The fluid conduit can at least partially extend from the housing and be configured to deliver medication within the medication source to a patient. The medication port can extending from an external surface of the housing and be configured to be coupled to a fluid outlet of a tubing set coupled to the medication source. The medication port can be fluidically and directly coupled to the fluid conduit. The at least one sensor can be disposed within the housing to generate information characterizing administration of the medication. The transmitter can be disposed within the housing to wirelessly transmit information generated by the sensor to a remote data collection system. The self-contained power source can be disposed within the housing to power the at least one sensor and the transmitter.

In yet a further variation, a method can include receiving, by at least one data processor, information from a medication delivery apparatus characterizing administration of medication to a patient, associating, by at least one data processor, the information with data specifying at least one medication and/or a volume of medication, and promoting the associated data. The medication delivery apparatus can include a housing, a fluid conduit at least partially extending within the housing and configured to deliver medication from the medication source to a patient via a parenteral fluid administration pathway, a medication port extending from an external surface of the housing and configured to be coupled to a tubing set coupled to the medication source, the medication port being fluidically and directly coupled to the fluid conduit, and at least one first sensor disposed within the housing to generate information characterizing administration of the medication for processing by a remote data collection system. Promoting the associated data can include persisting the associated data, loading the associated data, presenting the associated data in a display device, and/or transmitting the associated data to a remote computing system.

Computer program products are also described that comprise non-transitory computer readable media storing instructions, which when executed one or more data processor of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many advantages. For example, the current subject matter allows for compact fluid injection port systems that automatically identify administered medication and/or determine volume and/or type of administered medication. The fluid injection port is sufficiently small to be placed on a standard IV line (and to be self-supporting) allowing it to be used in multiple situations including on-site paramedic treatments, during ambulance delivery of patients, as well as medical facilities such as emergency rooms/intensive care units/operating rooms/general care. Moreover, as medical staff (e.g., doctors, nurses, paramedics, etc.) are accustomed to delivering medicine through Y-sites on IV lines, through catheters and needles, the current subject matter requires little, if any, behavior modifications while allowing for intelligent delivery of medication and logging of administered medications. In addition, the compact nature of the fluid injection port obviates the need for a larger tabletop or cradle unit which can be cumbersome during code blue or other emergency events and which can require much needed space (displacing other required equipment). In addition, the current subject matter utilizes a wireless interface and does not require wires for communication of information to a data collection system which could interfere with or complicate patient care activity. In addition, data received by the data collection system can be actively displayed in real-time providing clearly visible information to the medical staff keeping all informed and up-to-date. Furthermore, the current subject matter eliminates manual record keeping and other activities that can tend to detract from the needed attention to a patient. Automated record keeping provides accurate records and frees up the health care provider's time enabling improved patient care. Lastly, the current subject matter is advantageous in that the medication injection site can be disposable (thereby increasing patient safety).

The details of one or more variations of the subject matter described herein are set forth in the accompanying drawings and the description below. Other features and advantages of the subject matter described herein will be apparent from the description and drawings, and from the claims.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings:

FIG. 2A is a diagram illustrating a first variation of a medication injection site with a medication port flush with or disposed within a cavity of a housing;

FIG. 2B is a diagram illustrating a second variation of a medication injection site with a medication port extending outside a housing;

FIG. 3A is diagram illustrating a detailed view of a medication injection site as in FIG. 2A;

FIG. 3B is a diagram illustrating a side view of a medication injection site as in FIG. 3A;

FIG. 3C is a diagram illustrating a magnified cross-sectional view of elements in FIG. 3B;

FIG. 4A is a diagram illustrating a medication injection site with a medication container bearing an alternate information source to that of FIG. 3A;

FIG. 4B is a diagram illustrating a side view of a medication injection site as in FIG. 4A;

FIG. 4C is a diagram illustrating a magnified view of a medication container having an alternate information source as in FIGS. 4A and 4B;

FIG. 4D is a diagram illustrating a second magnified view of a medication container having an alternate information source as in FIGS. 4A and 4B;

FIG. 8A is a diagram illustrating a medication container having a radial information source as in FIG. 4A in greater detail;

FIG. 8B is a diagram illustrating an alternate location for a radial information source;

FIG. 8C depicts a magnified view of elements shown in FIG. 8A;

FIG. 8D is an alternate information source that fits around a portion of a medication container;

DETAILED DESCRIPTION

Figure 1:
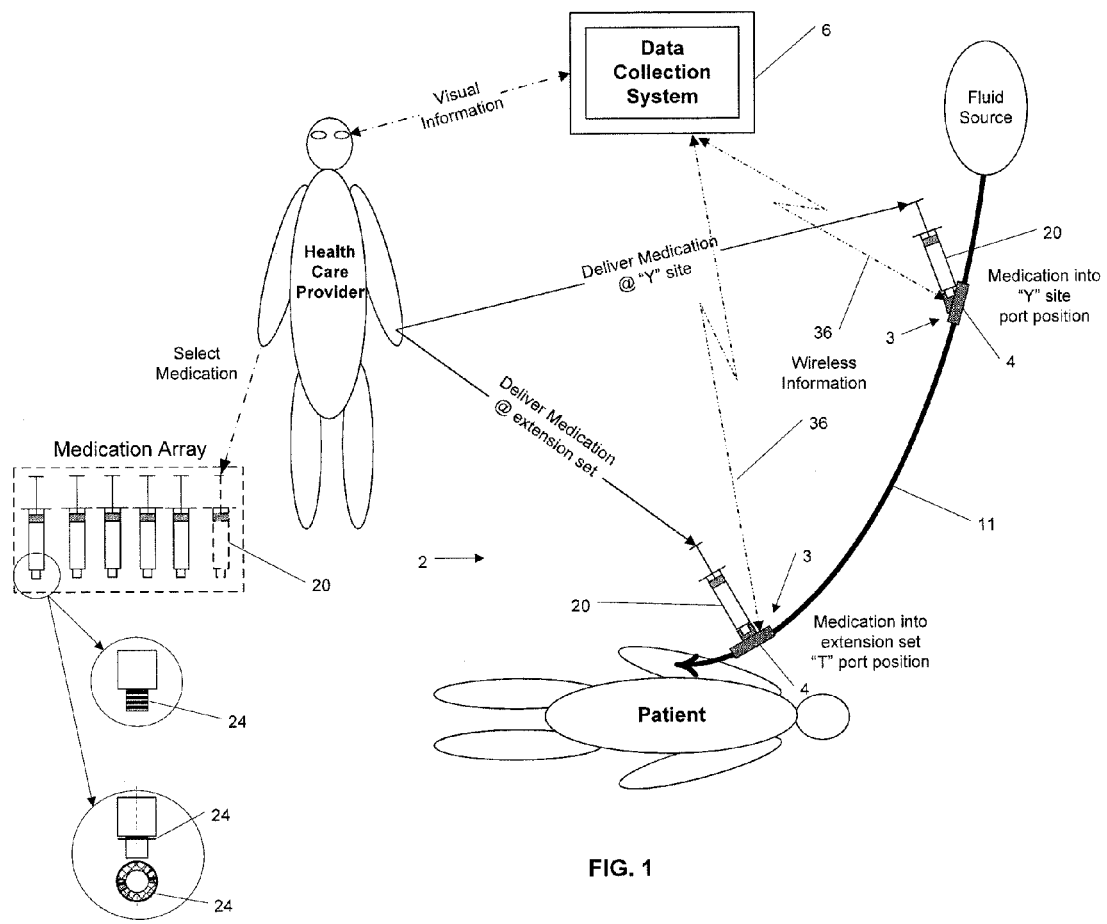
FIG. 1 is a diagram illustrating a healthcare provider using a medication injection site in connection with the care of a patient.

FIG. 1 is a diagram illustrating a system 2 in which a healthcare provider oversees the care of a patient. In particular, the healthcare provider selects and administers medications from a stock or an array of available medications. A medication container 20 can carry an information source 24 that provides detectable information indicative of the medication in the container and/or of the volume of the contents of the container. After selecting the appropriate medication, the healthcare provider delivers it to medication injection site 3. There can be several routes for parenteral administration of medications. One can be located on tubing set 11 connected to the patient. Tubing sets are frequently used for delivering fluids to patients and can provide a convenient access for manual medication injections as well as for controlled infusions. As shown in FIG. 1, the medication injection site 3 can be positioned at different locations along tubing set 11. In some implementations, the location can be close to the fluid source bag (e.g., saline bag, etc.) where the medication injection site 3 is affixed to or acts as a "Y" site on the tubing set 11. Here, pharmacy prepared admixtures can be attached to an IV tubing set. Alternately, medication injection site 3 can be in the form of an extension set located lower on tubing set 11 closer to the patient's infusion site. This site can be used for IV bolus injections where prompt medication delivery to the patient is important for acute care situations. Still other forms of medication injection site 3 can include direct bolus injection to a patient by attaching medication injection site 3 to a catheter or needle with little or no intermediate tubing (e.g., 10 cm or less, etc.). Here, medication is directly injected into the patient through a single fluid channel within medication injection site 3. Emergency medications, insulin, pain medications may use this administration method and are typically followed by a saline flush.

In any of the above medication injection site locations, a sensor at least partially enclosed by housing 4 of medication injection site 3 can detect the presence and type of medication container 20 and transmit information 36 via wireless communications to data collection system 6. Medication injections (from one or more medication containers 20) can be time stamped and recorded in a history log and/or added to the patient's medical records and/or billing records. The healthcare provider can view on a display of data collection system 6 which medication has been injected into the patient and when such medication was administered. Immediate display of information assists the healthcare provider in making further medication decisions for the care of the patient.

FIGS. 2A and 2B are diagrams illustrating medication injection site 3 with medication container 20 in a spatially separated state (FIG. 2A) and a coupled state (FIG. 2B). In this variation, the medication injection site 3 can include a first fluid channel 8 and a second fluid channel 10 (other channels may be included in some implementations). Housing 4 of medication injection site 3 can include both the first fluid channel 8 (continuous fluid channel connecting the fluid source to the patient) and the second channel 10 (injection port fluid channel) joining the first fluid channel forming an intersecting junction 15. The first and second fluid channels 8, 10 may be fully enclosed by the housing 4 or one or both may extend outwards from the housing (e.g., if the fluid channels 8, 10 comprise flexible tubing with connection adapters for coupling to further tubing). The first and second fluid channels 8, 10 are sometimes collectively referred to herein as a fluid junction element. In some variations, the fluid junction element can comprise a unitary element (e.g., injection molded material, etc.). With other variations, the fluid junction element can comprise a plurality of sections (i.e., it is non-unitary) and/or is integrated with the housing (e.g., sections of the housing form the fluid paths).

The first fluid channel 8 can extend from a first end 12 to a second end 14. The second fluid channel 10 can extend from an opening of medication port 13 at a distal end and can terminate at the first fluid channel 8 at intersection 15 intermediate the first end 12 and second end 14. The medication port 13 can be configured to fluidically couple to a fluid outlet 17 of medication container 20.

An identification sensor 18 can be at least partially disposed within housing 4 (i.e., the identification sensor 18 can be enclosed by the housing 4 or a portion of it can extend outwards from an outer surface of the housing 4, etc.) to generate information indicative of contents and/or volume of contents of medication container 20. In some variations, the identification sensor 18 can generate such information when fluid outlet 17 of medication container 20 is fluidically coupled to medication port 13. In other variations, the identification sensor can generate such information when fluid outlet 17 of medication container is adjacent to medication port 13. A transmitter 34 can be disposed within housing 4 and in communication with and/or coupled to identification sensor 18 to wirelessly transmit the information 36 generated by the identification sensor 18 to the remote data collection system 6. Examples of wireless transmission hardware and protocols can be utilized such as Bluetooth, Zigbee, Continue, Wireless USB, Wibree, IEEE 802 relevant standards (e.g., 802.11, 802.15, or 802.16, etc.) and other methods. The data transmissions can, in some implementations, be encrypted in order to ensure patient privacy and/or to comply with various laws relating to handling of medical data. The transmitter 34 can have such encryption capabilities or one or more additional chipsets can be incorporated within the medication injection site 3 to provide such encryption. The signal from identification sensor 18 can be processed and readied for transmission by sensor circuit 30. A self-contained power source 19 (e.g., battery or battery array, etc.) can be disposed within housing 4 to provide power for one or more of identification sensor 18, sensor circuit 30 and transmitter 34.

Housing 4 and/or the entire medication injection site 3 can have a shape and size enabling it to be hand-held by a first hand of a user while the user administers medication from medication container 20 via the fluid outlet 17 using his or her second hand. The housing 4 and/or the entire medication injection site 3, excluding any external tubing can, in some implementations have a largest dimension of 10 centimeters or less. In addition, the entire housing 4 and its contained components and/or the entire medication injection site 3 can be lightweight being less than 1 kg, and in some implementations, less than 100 grams and in some implementations less than 50 grams. The compact and/or lightweight nature of the medication injection site 3 allow it to be suspended below the fluid source at a Y-site (or to replace a Y-site) and supported by the tubing set 11 during use (see diagram of FIG. 10B). Alternately, the small size and weight can facilitate use on tubing set 11 closer to a patient's injection site and can be conveniently secured to the patient's arm (see diagram FIG. 2C).

In some implementations, housing 4 can be separated into two sub-housings (see diagrams FIGS. 15A, 15B, 15C, 15D). A reusable sub-housing 80 can house reusable elements (i.e., elements that can be safely used among several patients, etc.) while a disposable sub-housing 82 can house disposable elements (i.e., low-cost and/or sterile elements that are recommended for use in connection with a single patient, etc.). The sub-housings can be operatively coupled by connecting element 84 thus forming a fully functional injection site 3.

Housing 4 can be made of a rigid material that protects the component contained within the housing 4 from handling and fluids during use. Housing 4 can rigidly position and fix its contained components relative to each other. Housing 4 can be made by plastic injection molding a material such as polystyrene or polycarbonate to form one or more pieces of the housing. Sections of the housing 4, can in some implementations, form the first fluid channel 8 and the second fluid channel 10. In one variation, the entire housing 4, including the medication port 13, the first and second channels 8, 10 and internal components can be provided sterile with protective sterility covers on the first end 12 and the second end 14 of first fluid channel 8 as well as medication port 13.

All or some of the components of the medication injection site 3 can be selected so as to withstand conventional single use medical device sterilization processes such as EtO or radiation. The medication injection site 3 can be packaged with sterility covers in place in a peel-pouch kit configuration and provided to the user with a sterile fluid delivery pathway ready for use with sterile medications and/or fluids. Instruction for use and/or other identifying materials may be included with the medication injection site 3 to form a kit.

Removal of one or more of the sterility covers on medication injection site 3 can result in the self-contained power source 19 powering one or more of the transmitter 34 and the sensor circuit 30. Initial power-up sequences can synchronize communications between transmitter 34 and receiver 42 (see FIG. 5). Indicator 35 (see FIG. 5) can indicate readiness for medication delivery and data collection system 6 can indicate the start of medication record keeping. In some implementations LED emitter 32 can provide user readiness information similar to the function of indicator 35. LED emitter 31 can illuminate housing 4 and/or medication injection site 3 with a visual alert (e.g., blinking light, etc.) thus drawing user attention to the injection port and its readiness for operation. Later, when medication container 20 is coupled to medication injection site 3 LED emitter 31 (or indicator 35) can illuminate medication site 3 and the fluid outlet of medication container 20 in a steady ON state indicating successful fluid coupling and identification member detection. Other visual indicators such as combinations of blinking and/or steady ON can indicate various operational states of the injection port.

Figure 2C:
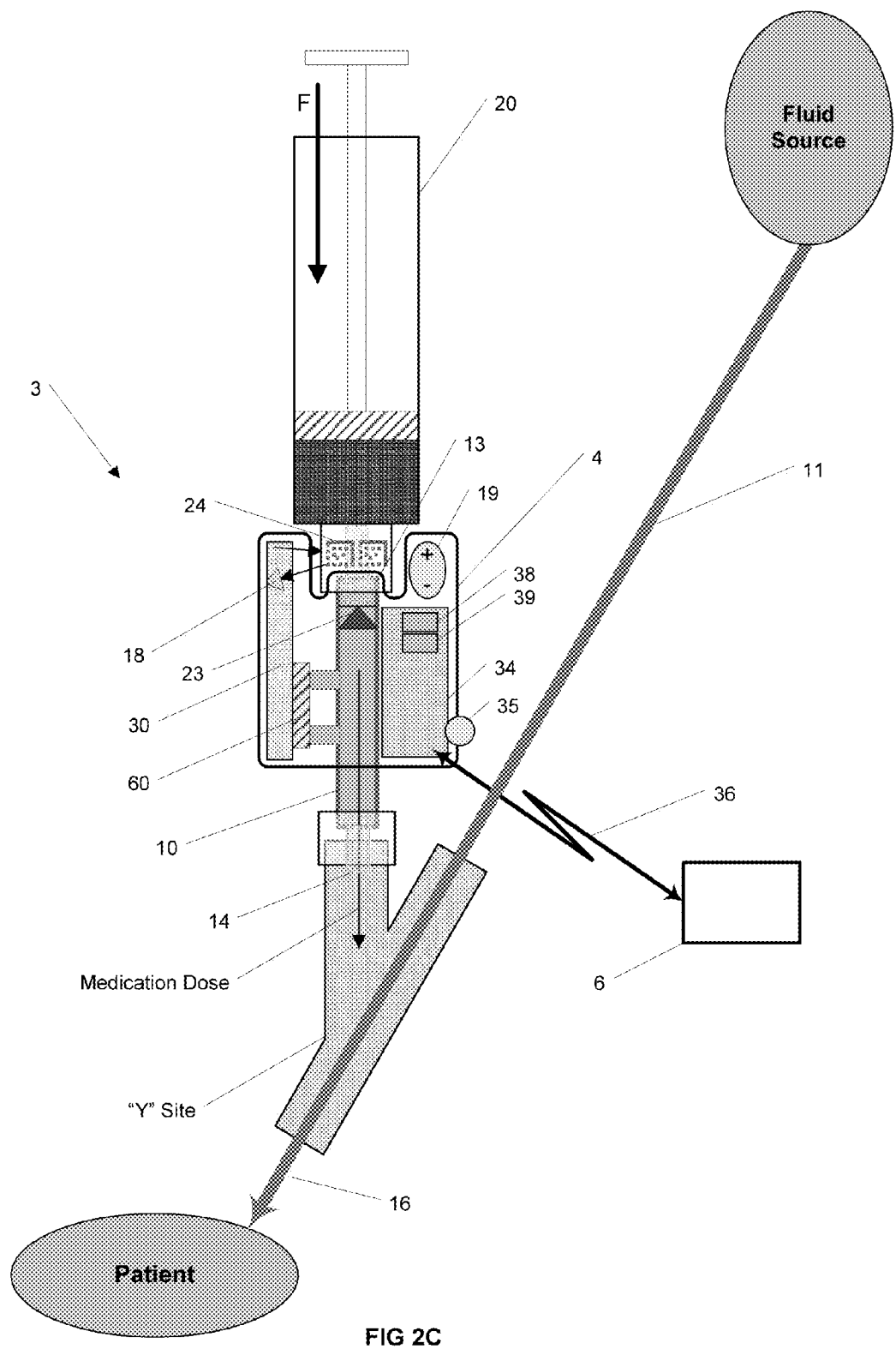
FIG. 2C is a diagram illustrating a third variation of a medication injection site with a medication port directly connected to a fluid delivery tubing set "Y" site.
Figure 2D:
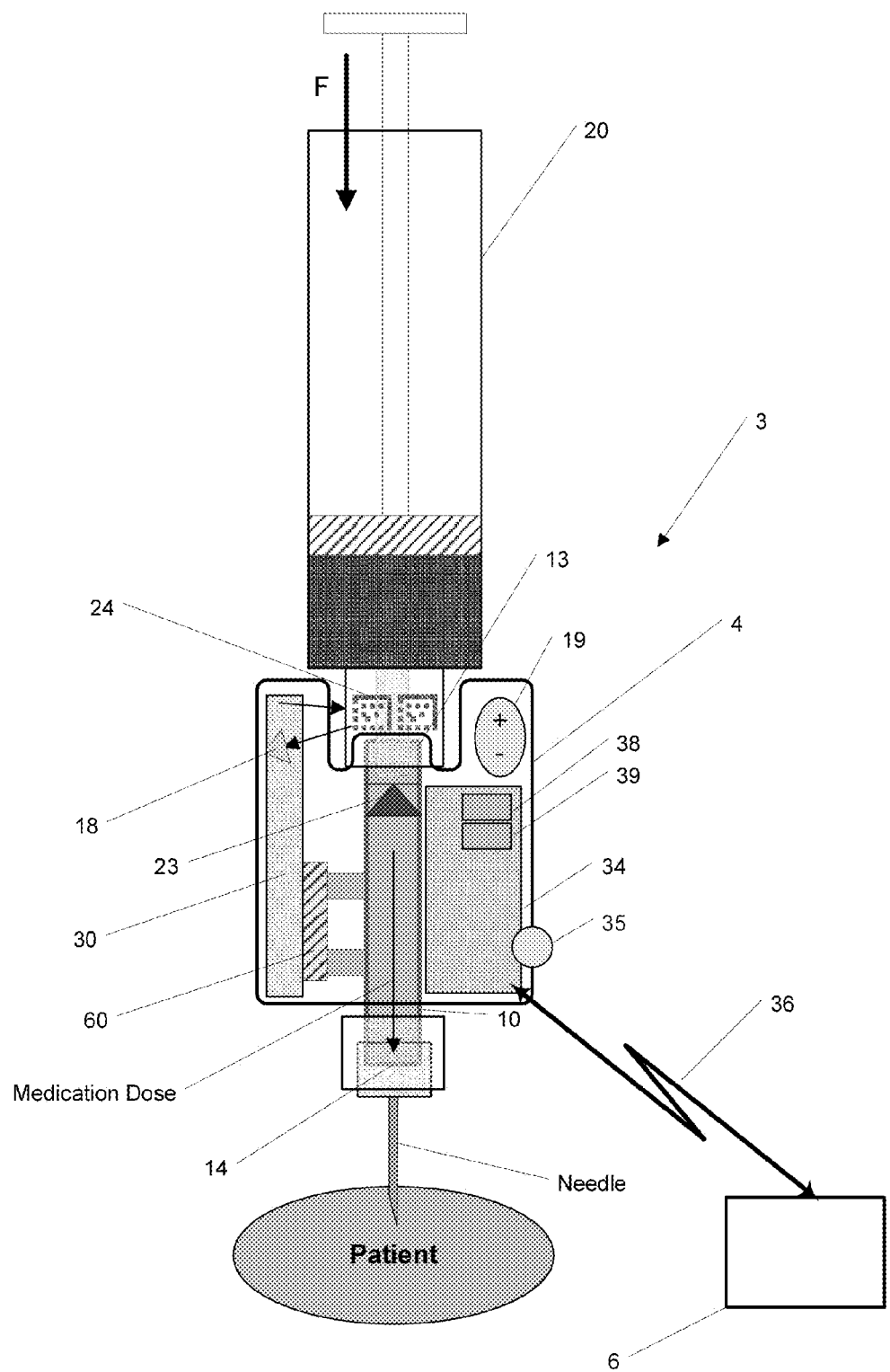
FIG. 2D is a diagram illustrating a fourth variation of a medication injection site with a medication port directly connected to a needle.

FIGS. 2C and 2D are diagrams illustrating medication injection site 3 with medication container 20 in a coupled state. In these variations, the medication injection site 3 does not include a first fluid channel 8 as part of injection site 3. Only the second fluid channel 10 is included. The second fluid channel 10 can be fully enclosed by the housing 4 or can extend outwards from the housing. Additionally, other elements can be included in housing 4 which will be described later. These can include check valve 23, indicator 35, memory element 38 and/or clock 39. Medication injection site 3 can be single use and fully disposable. In a different variation, medication injection site 3 can be separable into a disposable portion and a reusable portion as will be discussed in FIGS. 15A-15D.

FIG. 2C depicts housing 4 directly coupled to a "Y" site of an IV infusion tubing set 11. The second fluid channel 10 can extend from an opening of medication port 13 at a distal end and can terminate at the fluid outlet end 14. Second channel 10 can include a length of fluid delivery tubing to allow positioning of housing 4 for user convenience. The medication port 13 can be configured to fluidically couple to a fluid outlet 17 of medication container 20 (see FIG. 2A). Fluid channel 10 can include check valve 23 to limit fluid backflow from the "Y" site of infusion tubing set 11 into fluid channel 10. Alternately, check valve 23 can be included in medication port 13 and take the form of a swab-able needleless injection connector facilitating a luer connection from medication injection site 3.

An identification sensor 18 can be disposed within housing 4 to generate information indicative of contents and/or volume of contents of medication container 20. In some variations, the identification sensor 18 can generate such information when fluid outlet 17 of medication container 20 is fluidically coupled to medication port 13. In other variations, the identification sensor can generate such information when fluid outlet 17 of medication container is adjacent to medication port 13. A transmitter 34 can be disposed within housing 4 and in communication with/coupled to identification sensor 18 to wirelessly transmit the information 36 generated by the identification sensor 18 to the remote data collection system 6. The signal from identification sensor 18 can be processed and readied for transmission by sensor circuit 30. A fluid delivery sensor 60 can be included in housing 4 to provide information indicative of fluid flow and/or a volume characteristic. The signal from fluid delivery sensor 60 can be processed and readied for transmission by sensor circuit 30. Information 36 indicative of fluid flow and/or volume can be transmitted by transmitter 34 to data collection system 6. A self-contained power source 19 (e.g., battery or battery array, etc.) can be disposed within housing 4 to provide power for one or more of identification sensor 18, fluid delivery sensor 60, sensor circuit 30, transmitter 34 and indicator 35.

Housing 4 and/or the entire medication injection site 3 can have a shape and size enabling it to be hand-held by a first hand of a user while the user administers medication from medication container 20 via the fluid outlet 17 using his or her second hand. The housing 4 and/or the entire medication injection site 3, can in some implementations have a largest dimension of 10 centimeters or less. In addition, the entire housing 4 and its contained components and/or the entire medication injection site 3 can be lightweight being less than 100 grams, and in some implementations, less than 50 grams. The compact and/or lightweight nature of the medication injection site 3 allow it to be suspended below the fluid source attached to an upper Y-site and supported by the tubing set 11 during use. Alternately, the small size and weight can facilitate use on tubing set 11 attached to a lower "Y" site closer to a patient's injection site and can be conveniently secured to the patient's arm.

FIG. 2D depicts housing 4 directly coupled to a needle for direct injection to a patient. The second fluid channel 10 can extend from an opening of medication port 13 at a distal end and can terminate at the fluid outlet end 14. Second channel 10 can include a length of fluid delivery tubing to allow positioning of housing 4 for user convenience. The medication port 13 can be configured to fluidically couple to a fluid outlet 17 of medication container 20. Additionally, other elements can be included in housing 4 which will be described later. These can include check valve 23, indicator 35, memory element 38 and/or clock 39.

An identification sensor 18 can be disposed within housing 4 to generate information indicative of contents and/or volume of contents of medication container 20. In some variations, the identification sensor 18 can generate such information when fluid outlet 17 of medication container 20 is fluidically coupled to medication port 13. In other variations, the identification sensor can generate such information when fluid outlet 17 of medication container is adjacent to medication port 13. A transmitter 34 can be disposed within housing 4 and in communication with/coupled to identification sensor 18 to wirelessly transmit the information 36 generated by the identification sensor 18 to the remote data collection system 6. The signal from identification sensor 18 can be processed and readied for transmission by sensor circuit 30. A fluid delivery sensor 60 can be included in housing 4 to provide information indicative of fluid flow and/or a volume characteristic or a medication type composition sensor. The signal from fluid delivery sensor 60 can be processed and readied for transmission by sensor circuit 30. Information 36 indicative of fluid flow and/or volume and/or medication type can be transmitted by transmitter 34 to data collection system 6. A self-contained power source 19 (e.g., battery or battery array, etc.) can be disposed within housing 4 to provide power for one or more of identification sensor 18, fluid delivery sensor 60, sensor circuit 30, transmitter 34 and indicator 35.

The fluid delivery sensor 60 shown in FIG. 2D can be a medication composition sensor to provide verification of the type of fluid injected (the medication composition sensor can be one or more sensors that are separate and distinct from the fluid delivery sensor 60). Medication composition sensor 60 can be based on and include, but not limited to technologies such as: photometric analysis, electrometric analysis, chromatography, mass spectroscopy, physical property measurements, pH detection, viscosity indication, optical density indication, chemical indication, drug molecule indication, spectrophotometer measurement, HPLC detection, UV detection, fluid density measurement, specific gravity measurement, or parametric analysis based on a combination of the previously listed technologies. Alternately, or in combination with the above, the composition sensor 60 can be a combination of a number of measured parameters, including but not limited to the above parameters, that populate a table with values indicative of the medication. The table can be included in medication injection site 3 or data collection system 6. The table can be compared to a stored look-up table with a known set of parameter values for a specific medication type and concentration to determine the actual medication type and/or concentration of the fluid injected.

Housing 4 and/or the entire medication injection site 3 can have a shape and size enabling it to be hand-held by a first hand of a user while the user administers medication from medication container 20 directly to the patient through a needle. In another embodiment, the housing can have a size and shape enabling it to be used by one hand, either by securing it to a surface with pressure from the hand or utilizing a mounting fixture. Alternately, the needle shown in FIG. 2D can be inserted into a "Y" site of infusion set 11 as shown in FIG. 2C.

FIGS. 3A-C depict various features of the medication injection site 3. With reference to FIG. 3A, the first end 12 of first fluid channel 8 can be attached to a fluid source through tubing set 11 and the second end of first fluid channel 8 can be attached to a patient through tubing set 16. While tubing sets 11 and 16 are illustrated as being separate, some variations include a single tubing set extending through the housing 4. First fluid channel 8 can join first end 12 (i.e., fluid inlet) and second end 14 (i.e., fluid outlet) forming a fluid path inside housing 4. First fluid channel 8 can be joined by second fluid channel 10 at intersection 15 for the administration of medication from container 20. Intersection 15 can be positioned such that the relationship between the first fluid channel 8 and the second fluid channel 10 is a right angle as shown in FIG. 3A substantially forming a "T"-shape. Alternatively, the channels 8, 10 can be positioned to form an acute angle. In some implementations, the angle is such that the first fluid channel 8 and the second fluid channel 10 form a "Y" shape.

A check valve 22 can be situated in the first fluid channel 8 upstream of intersection 15 to prevent fluid backflow upstream into the fluid source when the medication container 20 is delivering fluid into medication port 13. The second fluid channel 10 can contain a check valve 23 to prevent fluid flow from the first fluid channel 8 from flowing into the second fluid channel 10.

Medication container 20 can be a syringe or other medication container such as a vial with compatible fluid coupling of outlet 17 on medication container 20 to medication port 13 (e.g., a slip luer, luer-lock fitting, a vial adapter spike, etc.). Medication container 20 can include information source 24 located on the fluid outlet attachment tip of container 20. Such information source 24 can, in some implementations be affixed, integrated, secured, and/or adhered to a portion intermediate the fluid outlet of medication container 20 and a barrel portion of container 20. Such intermediate portion can be tapered and/or planar. The information source 24 can be an integrated feature of the medication container 20 such as etched or molded features. The information source 24 can alternatively be adhered to the fluid outlet attachment tip of medication container 20 (i.e., information source 24 can be a label, etc.). In addition, the information source 24 can be a separate element that extends around the fluid outlet of the medication container 20 (applied either during manufacture of the medication container or subsequently whether during distribution or use).

When provided to a user, medication port 13 can be protected by port cover 21. Prior to use, the port cover 21 maintains medication port 13 in a sterile condition. Similarly, when provided as an extension set (i.e., medication injection site 3 includes added tubing that increases functional capability of fluid administration line and extends the fluid tubing set 11), sterility covers can be provided on the first end 12 and the second end 14 of the first channel 8. When used, the medication injection site 3 can be connected to the fluid source by removing the sterility cover on the first end 12 and attaching tubing set 11. Secondly, the sterility cover can be removed from the second end 14, fluid flow is then established through first fluid channel 8 and then second end 14 is connected to tubing 16. Tubing 16 can then be attached to a patient's catheter for delivery of fluids and medications.

The identification sensor 18 can include an optical emitter/detector pair 31 with horizontal orientation on sensor 18 that detects encoded information contained on information source 24 (a sleeve around the fluid outlet of the medication container 20) parallel to the fluid outlet axis. The identification sensor 18 can comprise a plurality of sensors to detect information source 24. In some variations, the identification sensors can be sensors such as optical, magnetic, mechanical, conductive, switchable RFID and/or proximity sensors. In other variations, identification sensor 18 can be optical and can include an illumination source (emitter) such as an LED and a detection source (detector) such as a camera (CCD). Sensor circuit 30 can provide signal processing and connects identification sensor 18 to transmitter 34. The identification sensor 18 can be directly coupled to power source 19.

FIG. 3B depicts a side view of medication injection site 3. Housing 4 is sized and shaped to easily fit into a user's hand. The location of medication port 13 can be anywhere along the length of first channel 8 and conveniently positioned for ease of use.

FIG. 3C is an enlarged view of medication port 13 showing identification sensor 18 having a concentric (or at least partially concentric) configuration so that it can surround information source 24 on the outlet 17 of medication container 20. When medication container 20 is coupled to the medication injection site 3, outlet 17 is fluidically coupled to medication port 13 and information source 24 is simultaneously positioned for detection within and in close proximity to identification sensor 18.

FIGS. 4A, 4B, 4C and 4D depict an alternate implementation of information source 24 and identification sensor 18. FIG. 4A depicts a cross-sectional view of medication container 20 coupled to a medication injection site 3. FIG. 4B is a side view. The medication injection site 3 can include an optical emitter and detector pair 31 positioned and configured to optically detect encoded information 29 on information source 24. Information source 24 can take the form of a disk or other element with an opening mounted over the fluid outlet perpendicular to the fluid outlet axis. Information source 24, when taking the shape of a disk, can be substantially planar and include an inner opening 27 (see, e.g., FIGS. 4A, 4C, 4D) that corresponds to fluid outlet 17 of medication container 20. Such an information source 24 can be mounted to medication container 20 so that inner hole 27 is concentric with fluid outlet 17 (and positioned so that medication container 20 can still be coupled to medication injection site 3 and medication can be delivered).

As shown in FIGS. 4C and 4D when used, information source 24 and medication container 20 can be rotated together clockwise to complete the fluid coupling of fluid outlet 17 to medication port 13. Barcode indicia 29 are also correspondingly rotated. The optical emitter/detector pair 31 can scan (i.e., illuminate and detect) the rotated barcode indicia 29 and extract the identifying information. Such identifying information can then be passed from sensor circuit 30 to transmitter 34 for transmission.

In some implementations, the identification sensor 18 can include a series of more than one sensor to detect information source 24. In addition, the identification sensors can be other types of sensors such as optical, magnetic, mechanical, conductive, switchable RFID and/or proximity sensors. With non-optical arrangements, the corresponding information source 24 and the detector 31 would be correspondingly modified. For example, if information source 24 comprises a magnetic strip, detector can be a magnetic strip reader. In addition, sensor circuit 30 provides signal processing and connects identification sensor 18 to transmitter 34.

Figure 5:
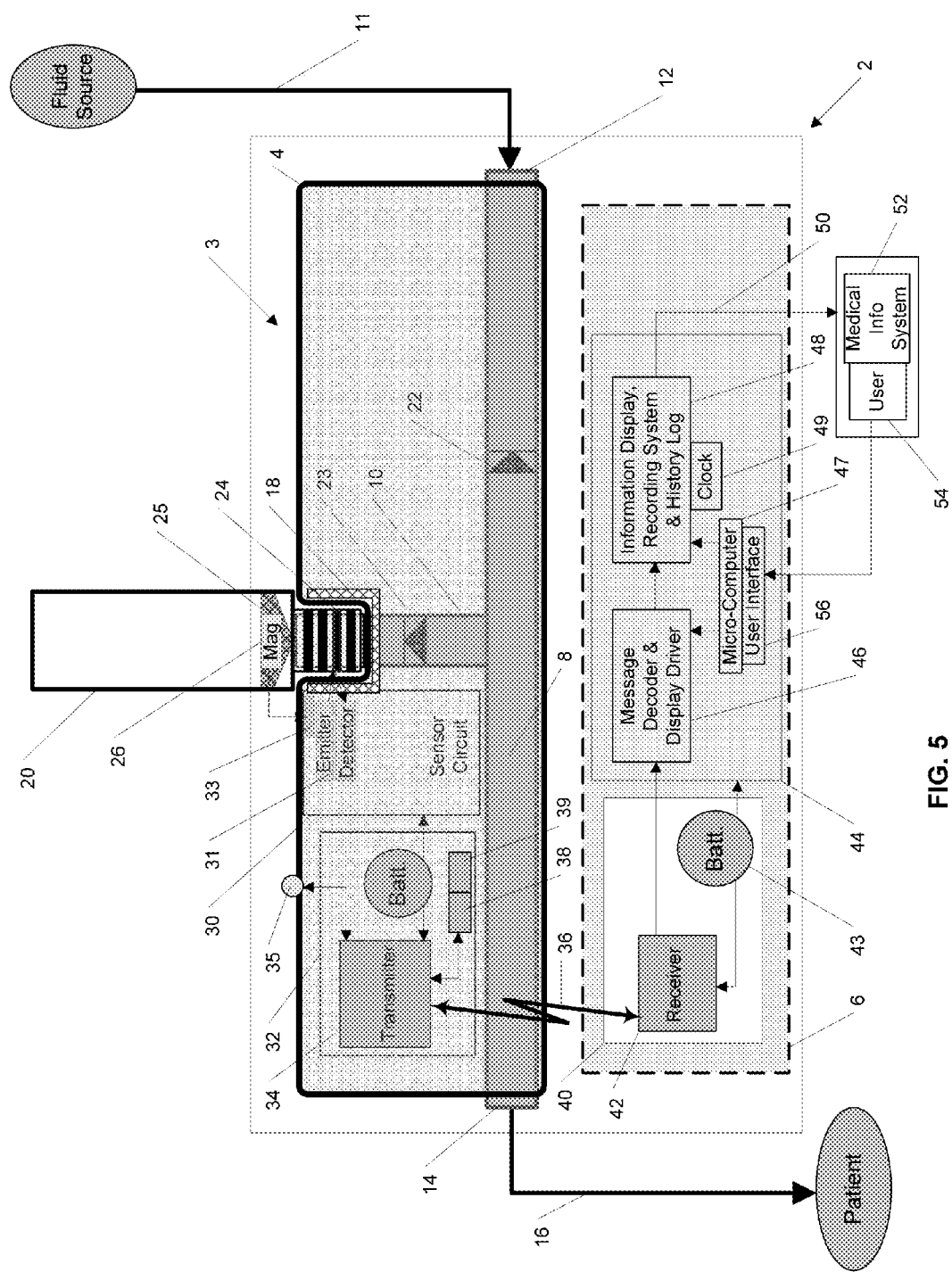
FIG. 5 is a diagram illustrating a medication injection site and a data collection system.

FIG. 5 depicts additional elements of system 2 including a medication injection site 3 with a centrally located second fluid channel 10, further elements contained within data collection system 6 and connection to a medical information system 52. Medication injection site 3 can include information processing and transmission circuit 32. Signals from sensor circuit 30 can be processed for transmission to data collection system 6 by circuit 32. Sensing circuit 30 can generate one or more signals in response to connection of medication container 20 to medication port 13. When identification sensor 18 detects connection of medication container 20 a visual and/or audible indicator 35 can be actuated to provide feedback to the user of proper connection. Transmitter 34 can transmit information 36 to receiver 42 contained in data collection system 6. When transmitter 34 transmits information 36 to receiver 42 a visual and/or audible indicator 35 can be actuated to provide feedback to the user of proper transmission.

The sensor circuit 30 can contain a Hall Effect sensor 33 that detects the completion of medication administration when magnetic indicator 26 is in close proximity to sensor 33. Alternatively, sensor 33 and indicator 26 can be optical, mechanical, conductive and/or or proximity sensor/detector pairs and provide a medication administration complete signal to circuit 32. In this case, a second information transmission 36 can be sent to receiver 42 in response to a signal from sensor 33. When transmitter 34 transmits information 36 to receiver 42 a visual and/or audible indicator 35 can be actuated to provide feedback to the user of proper transmission of the completion of medication administration.

Medication delivered from medication container 20 can flow via outlet 17 into the second fluid channel 10, past check valve 23 and into first fluid channel 8. Fluid from the fluid source enters first fluid channel 8 at first end 12, flows past check valve 22 and out to the patient through second end 14 and tubing 16.

Data collection system 6 receives information 36 (e.g., packetized data, etc.) from transmitter 34 within the medication injection site 3. In one variation, data collection system 6 can include a personal computer (see FIG. 14A). In another variation, the data collection system 6 can be small, light weight and configured to be stand-alone with a self-contained power source 43 (see FIG. 14B). The data collection system 6 can be portable so that it can, for example, provide medication administration information for emergency medical services personnel in the field or it can be used on mobile crash carts, automated medication dispensing units or other medication storage systems by health care providers within a hospital, other healthcare facility or within a homecare environment. In one implementation, after medications are delivered (or during delivery) and the health care protocol is complete data collection system 6 can be connected (e.g., via a web service, wirelessly, or direct connection, etc.) to medical information system 52 for records transfer and/or data storage and/or patient billing, etc.

The data collection system 6 and/or the medication injection site 3 can initiate wireless exchange of information. Appropriate discovery/handshaking message exchanges are used to initiate communications (whether when the medication injection site 3 is first used or when there is an interruption of communications, etc.). The medication injection site 3 can interface with multiple data collection systems 6 at one time or simply pass information from a first data collection system 6 to subsequent data collection systems 6 (using, for example, memory resident in the medication injection site 3 as described below).

Within data collection system 6, information received by receiver 42 is sent to and processed by circuit 44. Circuit 44 contains a message decoder and display driver circuit 46, a micro-computer 47, an information display and recording system 48 and clock 49. Information received is time stamped by clock 49, logged into memory and displayed by circuit 48. Information displayed and recorded can include one or more of: the type and amount of medication delivered, time of medication administration, sequence of medications delivered, prompting messages providing real-time feedback to the healthcare provider on prior medications delivered, prompting messages for future medications to be administered with proposed protocol administration times, time since the medication was administered and other instructive information for conducting the health care protocol.

Display and recording system 48 can receive messages and generate a record documenting the time sequence of medication injections based upon signals received from sensor circuit 30. Display and recording system 48 can, in some variations, include a report generator capable of sending report information 50 to a medical information system 52. A user 54 can interact with micro-controller 47 via user interface 56 to provide additional information to the display and recording system 48. Additionally, user 54 can edit the report, add non-medication administration information to the report and complete printing or filing of the report to a medical information system 52. Medical information system 52 may be coupled to a local network and/or accessible via the Internet.

Display and recording system 48 can take the received information 36 and combine it with time information from clock 49 to generate a time stamped information log. Computer system 47 can receive the time stamped information for each medication injection. The medication information included in the time stamped log file can include, but is not limited to, type of medication, volume of medication injected, expiration date of the medication, medication manufacturer's information and user edited report information. Such information can be integrated with medical files for the patient and/or submitted to a patient billing system (e.g., by web service, etc.).

The message decoder and display driver circuit 46 can convert each signal into an encoded value indicative of the medication administration. The encoded value can then be provided to computer system 47 that decodes the value and provides the user with understandable information about the injections for editing.

In some implementations, the medication injection site 3 can contain memory 38 to store medication administration data. The data can include a sequential record of each medication administration made through medication injection site 3. Timer 39 provides time count data to memory 38 separating each successive medication administration data element. Situations that can occur necessitating the use of memory 38 and timer 39 include: failure of data collection system 6, inadvertent user failure to activate data collection system 6, transfer of a patient from one data collection system 6 to another during transfer of the patient to different health care providers (field emergency medical service care provider to ambulance care provider to hospital emergency room care provider, etc.). In these situations the patient's medication administration data is stored in memory 38 and can be recalled later by a different data collection system 6. The memory 38, in some implementations, can be removable allowing it to be accessed by a computing system. For example, the memory 38 can be part of a USB card allowing it to be removed and accessed by a separate computing system. In some variations, the memory 38 can store software to either launch a local application on such separate computing system or to launch a particular web site or initiate a web service. In either of such scenarios, the patient data can be transported for storage and/or display on such separate computing system (or to another computing system remote from such separate computing system).

Various types of medication containers 20 can be used with the medication injection site 3, provided, that the fluid outlet 17 of the medication container can couple to the medication port 13. FIGS. 6A-8C illustrate various arrangements such as syringes and reverse syringes. Other containers (not shown) can be in the form as discussed earlier.

Figure 6A:
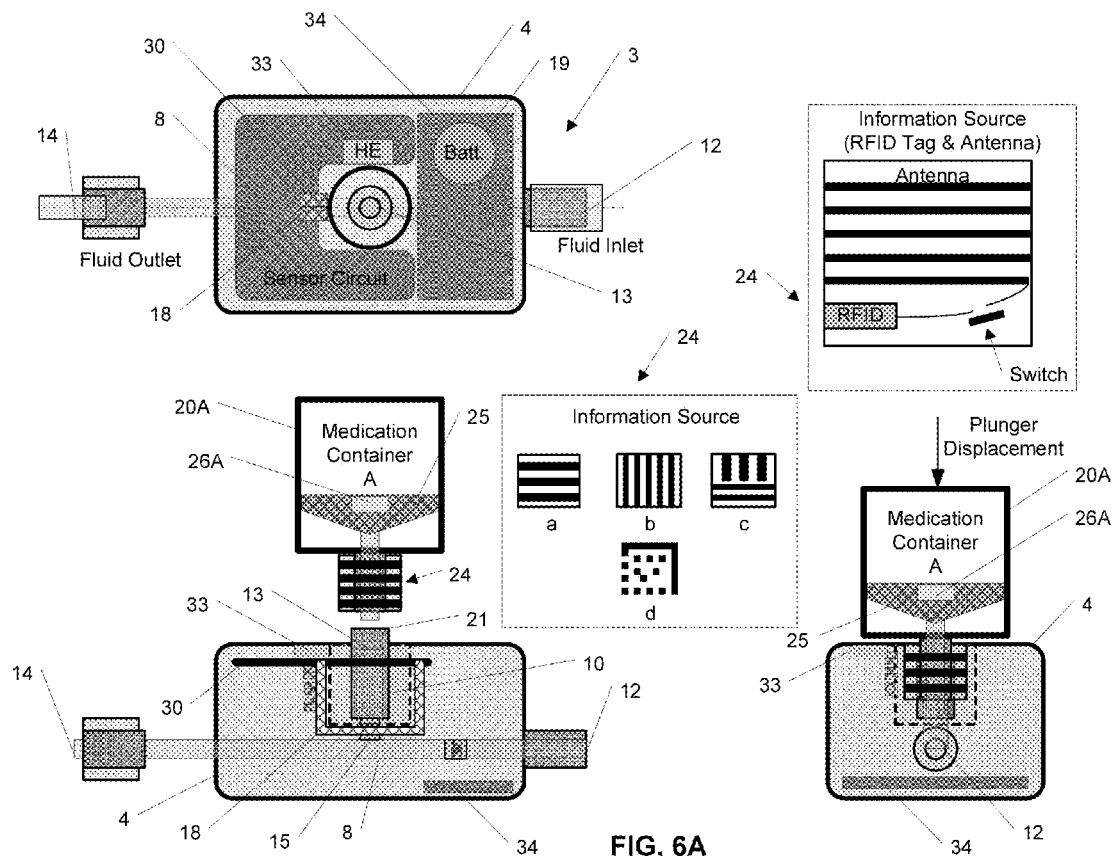
FIG. 6A is diagram illustrating a medication container containing an information source that can be optically detected.
Figure 6B:
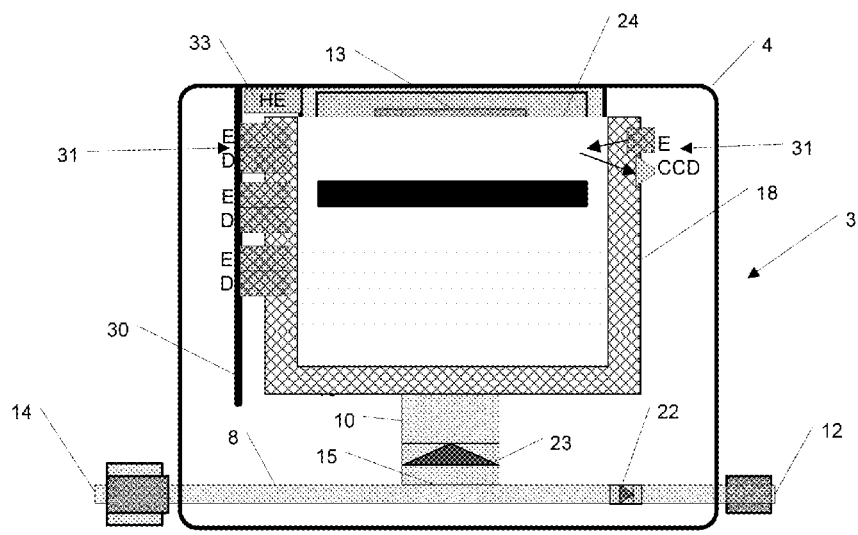
FIG. 6B is a diagram illustrating a magnified view of elements shown in FIG. 6A.

FIGS. 6A and 6B depict a medication injection site 3 with some elements removed for illustration purposes. FIG. 6A illustrates top and front views of housing 4 to the left with medication container 20A about to be coupled to medication port 13. A side view is depicted on the lower right with medication container 20A fully engaged with medication port 13. Fluid inlet first end 12 and fluid outlet second end 14 can be connected by first fluid channel 8. Fluid inlet 12 and fluid outlet 14 can be a slip luer, luer-lock or other fluid delivery fitting connectors and are typically fitted with sterile protective caps prior to use. Second fluid channel 10 can join first fluid channel 8 at intersection 15 Medication port 13 is initially provided for use with a sterile barrier cap 21 which is removed immediately prior to medication injection. Alternately, medication port 13 can be a swab-able needleless injection connector facilitating a luer connection from a syringe or other medication container 20. In some variations, the medication container 20 can include a needle or an outlet port adapter which acts as the outlet 17 which in turn is fluidically coupled to the medication port 13.

The housing 4 can at least partially enclose identification sensor 18, sensor circuit 30, transmitter 34 and a common power source 19 (battery, battery array, etc.). Sensor circuit 30 can provide for one or more identification sensors 18 (and/or 218 in FIG. 17) to detect information from medication information source 24 (and/or complementary information source 224 in FIG. 17). Transmitter 34 can process the sensor signals and transmits them to a data collection system 6.

In FIG. 6A medication container 20A can be a syringe with a fixed medication container and a slidable plunger 25 which moves during medication administration. Medication container (A) 20A can have a medication information source 24 affixed on the tip. There can be a number of variations (a, b, c, d) for information source 24. Information source 24a can contain information (e.g., readable data, etc.) indicative of the medication in one or more horizontal bands. Information source 24b contains information indicative of the medication in one or more vertical bands. Information source 24c contains information indicative of the medication in a combination of one or more horizontal and vertical bands. Information source 24d can contain information indicative of the medication in one or more dots in a two dimensional dot matrix pattern.

Additionally, plunger 25 can contain a ferric material 26A that can be detected by a magnetic sensor 33. The ferric material 26A can be a magnet or other type iron material matched with ferric material type sensor 33. When the medication delivery is completed plunger 25 with ferric material 26A comes into close proximity with sensor 33 and a medication administration complete signal is sent to circuit 32. Transmitter 34 then relays the information to receiver 42 for data collection. Other materials/devices may be used to detect relative position of the plunger 25.

With reference to the upper right portion of FIG. 6A, information source 24 can be an RFID tag with an antenna that can be connected or disconnected by a switch. With this arrangement, a switchable RFID tag information source 24 can be provided with the antenna disconnected. When medication container 20 is connected to medication port 13 the antenna becomes connected (switched ON) and the information source 24 can be read by an RFID reader identification sensor 18 within housing 4.

FIG. 6B is a magnified view showing a fully engaged information source 24 in close proximity to emitter (E) and detector (D) elements of identification sensor 18 shown on the left or emitter LED (E) and detector camera (CCD) elements 31 of identification sensor 18 shown on the right and Hall Effect sensor 33 all contained within the housing 4.

Figure 7A:
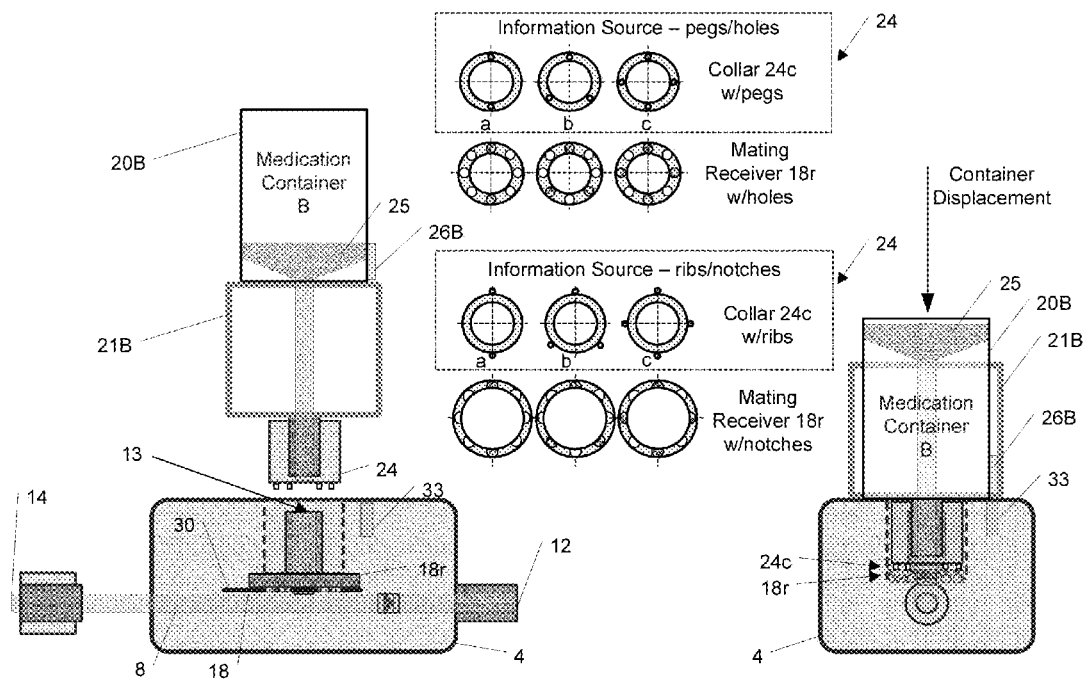
FIG. 7A is a diagram illustrating a medication container containing an information source that has mechanical features.
Figure 7B:
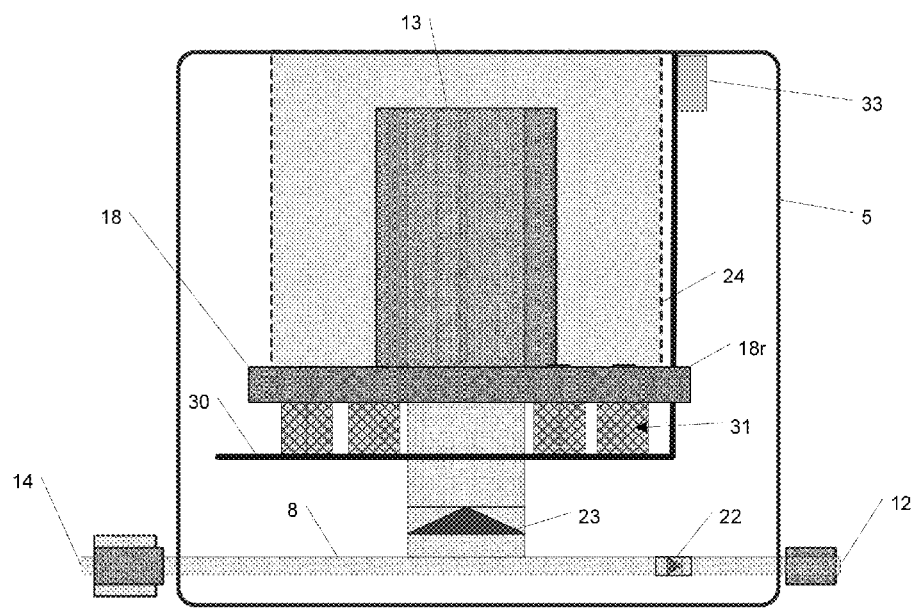
FIG. 7B is a diagram illustrating a magnified view of elements shown in FIG. 7A.

FIGS. 7A and 7B illustrate medication container 20B and injector housing 21B being a reverse syringe design wherein plunger 25 remains fixed relative to the motion of medication container 20B during medication administration. FIG. 7A on the left shows the medication container 20B with medication information source 24 affixed on the luer fitting tip before connection to medication port 13. Similar to medication container 20A, there can be a number of mechanical embodiments (a, b, c) for information source 24 on medication container 20B. Additionally, medication container 20B can contain an indicator 26B that can be ferric material that can be detected by magnetic sensor 33. The ferric material 26B can be a magnet or other type iron material matched with ferric material type sensor 33. Other types of indicators such as optical, capacitive, mechanical, etc. which are not ferric based can be used to indicate the completion of medication administration. When the medication delivery is completed as shown to the right medication container 20B with ferric material 26B comes into close proximity for detection by sensor 33 and a medication administration complete signal (or other data) can be sent to circuit 32. Transmitter 34 then relays the information to receiver 42 for data collection.

Indicator 26B can, in some implementations, be a switchable RFID tag with an antenna that can be connected or disconnected (see FIG. 6A). In this variation, an RFID tag indicator 26B can be provided with the antenna disconnected. When medication container 20B is fully displaced the antenna can become connected (switched ON) and the medication delivered indicator 26B can be read by an RFID reader within sensor circuit 30.

FIGS. 7A and 7B illustrate a variation in which information source 24 comprises a collar 24c with mechanical indicator pegs. FIG. 7A illustrates top and front view of housing 4. As shown to the left, medication container 20B is about to be coupled to medication port 13. A side view is depicted in the lower right such that medication container 20B is fully engaged with medication port 13. Collar 24c can have one or more indicator pegs arranged such as to indicate the type of medication contained in medication container 20B. Any number of pegs and/or peg patterns (a, b, c) can be used as an indication of the type of medication contained. Housing 4 can include a receiver identification sensor 18r that has opening holes to receive the pegs on collar 24c. Any number of opening patterns (a, b, c) can be used as an indication of the type of medication contained, the volume of medication, and/or expiration data. When properly engaged, pegs on collar 24c mate with receiver identification sensor 18r openings and form the medication information transfer. The pattern indicated is detected by identification sensor 18 and a signal can be sent to circuit 32. Transmitter 34 can then relay the information to receiver 42 for data collection.

Information source 24c can alternatively have external indicator ribs (or similar type of protrusions). Information source 24c can have one or more indicator ribs arranged such as to indicate the type of medication contained in medication container 20B or other relevant information. Any number of ribs and/or rib patterns (a, b, c) can be used as an indication of the type of medication contained. Housing 4 can include a receiver identification sensor 18r that has opening notches to receive the ribs on information source 24c. Any number of opening patterns (a, b, c) can be used as an indication of the type of medication contained. When properly engaged, ribs on information source 24c can mate with receiver identification sensor 18r notches or other features. The pattern indicated by receiver information source 18r can be detected by identification sensor 18 so that a signal containing data characterizing the medication container 20 is sent to circuit 32. Transmitter 34 then relays the information to receiver 42 for data collection.

FIG. 7B is diagram illustrating a magnified view showing a fully engaged information source 24 in close proximity to emitter (E) and detector (D) elements 31 of sensor circuit 30 and sensor 33 all contained within the housing 4. Information source 24c can have protrusions (in this case four pegs) protruding from the collar 24c. Receiver identification sensor 24r can mate with pegs on information source 24c facilitating detection of the medication information by emitter (E) and detector (D) sensors mounted on sensor circuit 30. Additionally, sensor 33 is shown located on the uppermost part of housing 4 for the detection of ferric material 26B.

FIGS. 8A, 8B and 8C depict a variation of information source 24. FIG. 8A depicts information source 24 formed as a flat disk mounted to the fluid outlet 17 of medication container 20. Information sensor 18 can be oriented vertically and detect information when medication container 20 is rotated about the fluid outlet axis. Information can be encoded using optical or magnetic methods. In one implementation, the information source 24 can carry a radial barcode pattern 29. Emitter/detector pairs 31 can detect information and signals can be provided to sensor circuit 30 that characterize the medication container 20. An alternate information source (a two dimensional barcode) and emitter/detector pair 31 (LED and Camera CCD) is shown in FIG. 4D

FIG. 8B depicts information source 24 as a cylindrical/circumferential band having an outer surface that is mounted to the fluid outlet 17 of medication container 20. Information sensor 18 can be oriented horizontally and detect information when medication container 20 is rotated about a fluid outlet axis. Information can be encoded using optical or, magnetic methods. The band can have a barcode pattern that extends along the cylindrical surface at a constant radius. Emitter/detector pairs 31 can detect information and signals characterizing the medication container 20 can be provided to sensor circuit 30.

FIG. 8C depicts a magnified view of elements shown in FIG. 8A. An attachment material 37 can be interposed between medication container 20. The attachment material 37 can configured to be releasable from a first medication container and re-attached to a second medication container. The attachment material can be an adhesive material or a snap in place mechanical material. Alternately the information source 24 (disk or cup) can include gripping or latching type teeth on the inner diameter 27 of information source 24. This feature can be used when an original medication container 20 (medication vial) is provided without a fluid outlet and a second medication container 20 (syringe) is used to withdraw medication from the first medication container 20 (vial) for use with medication injection site 3. The information source 24 originally provided with the first medication container (vial) can be removed and then attached to the second medication container (syringe) during the medication transfer process. The contents of the second medication container 20 can be injected into the medication port 13 and information can be detected by information sensor 18.

The medication container can be a first medication container and the identification member can be releasably secured to the medication container to allow it to be removed for placement on a second medication container. The identification member can bear an attachment element allowing it to be removed from the first medication container and affixed to the second medication container. Transfer of the identification member from the first medication container to the second medication container can be completed during the process of transferring the medication from the first medication container to the second medication container.

FIG. 8D depicts an alternate information source 24 in the shape of a cup similar to information source 24 in FIG. 8B except that the information source 24 cup fits around the luer tip of the medication container outlet and can be detected by information sensor 18 mounted horizontally as shown in FIG. 8C. Information source 24 cup can attach and detach in a similar way as information source 24 disk to attachment material 37.

Figures 9A, 9B, 9C:
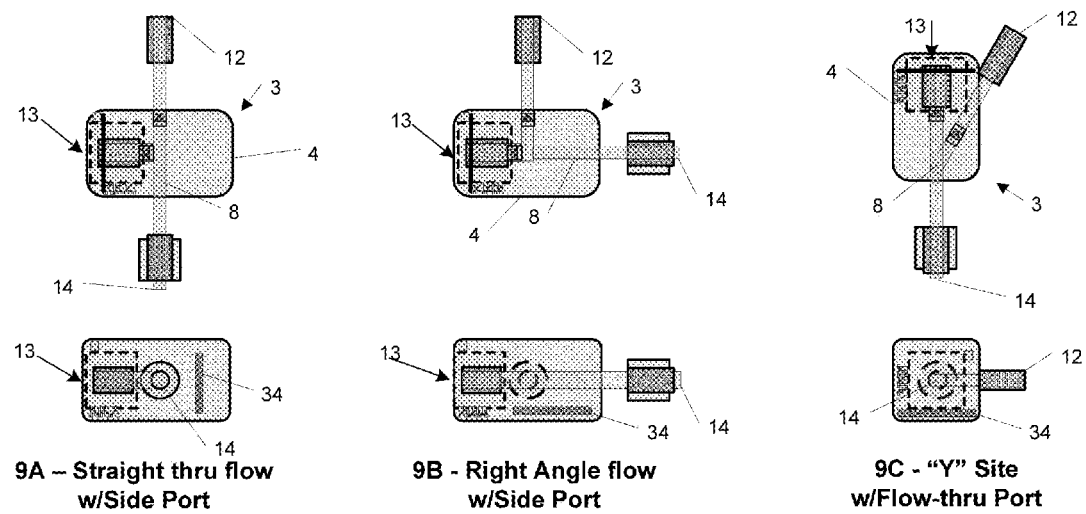
FIG. 9A is a diagram illustrating a medication injection site with a linear first fluid channel intersected by a second fluid channel at right angle.
FIG. 9B is a diagram illustrating a medication injection site with a first fluid channel intersected by a second fluid channel at right angle and a medication port coupled to the intersection of the first fluid channel and the second fluid channel.
FIG. 9C is a diagram illustrating a medication injection site with a first fluid channel intersected by a second fluid channel at an acute angle.

FIGS. 9A, 9B and 9C depict top and front views of alternate construction embodiments of the fluid junction elements and housing 4. FIG. 9A shows housing 4 with a straight through first fluid channel 8 with a side access for medication port 13. FIG. 9B shows housing 4 with a right angled first fluid channel 8 with a side access for medication port 13. FIG. 9C shows housing 4 with a "Y" first fluid channel 8 and a straight through medication port 13. Various other configurations can be constructed with different positioning of inlet 12, outlet 14 and medication port 13 to facilitate any requirements of the clinical set-up, orientation of hospital equipment, and/or medical practitioner preference. FIG. 9A depicts a configuration that is a typical extension set facilitating an in-line attachment from tubing set 11 to a patient's catheter. FIG. 9B depicts a configuration that facilitates connection to a manifold (outlet 14) and allows straight through injections into medication injection port 13. FIG. 9C depicts a configuration that is a typical "Y" site arrangement facilitating location of medication port 3 on tubing set 11.

Figure 10A:
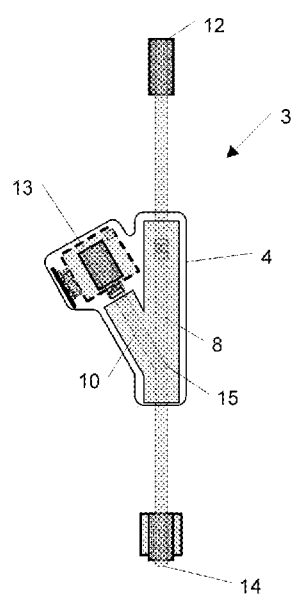
FIG. 10A is a diagram illustrating a fluid delivery tubing set.
Figure 10B:
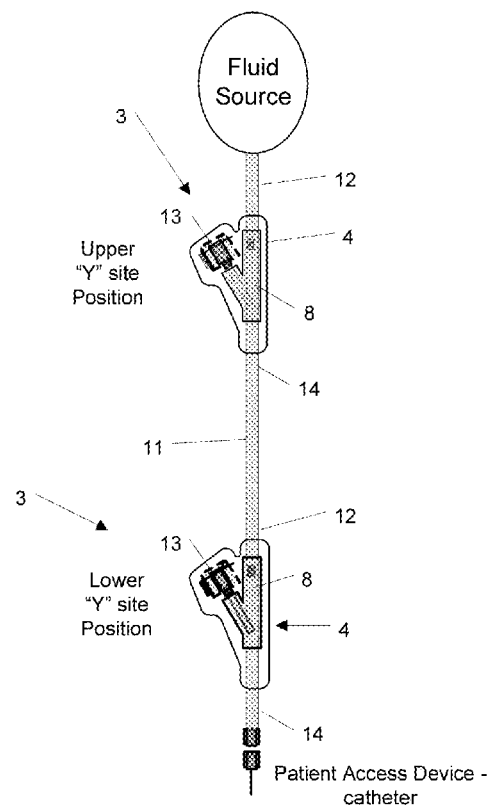
FIG. 10B is a diagram illustrating different locations for a fluid delivery tubing set as in FIG. 10A.

FIGS. 10A and 10B depict alternate variations for housing 4 as mounted on fluid delivery tubing sets. FIG. 10A depicts a "Y" site adapter configuration. Here inlet 12 and outlet 14 can be separated by an extended conduit 8 to form an extension set. FIG. 10B depicts a complete fluid delivery tubing set with inlet 12 being a fluid bag spike and outlet 14 a connector to a patient access device. The housing 4 can be located near the fluid source bag at an upper "Y" site or nearer the patient at a lower "Y" site location. Multiple configurations (e.g., two or more medication injection sites used for a single patient, etc.) allow for greater access for tubing set medication injection during medical procedures when several practitioners are simultaneously working on a patient (and access to one particular medication injection site may be impeded). Other configurations can be utilized as a function of the clinical setting physical space and access to the tubing set.

Figure 11A:
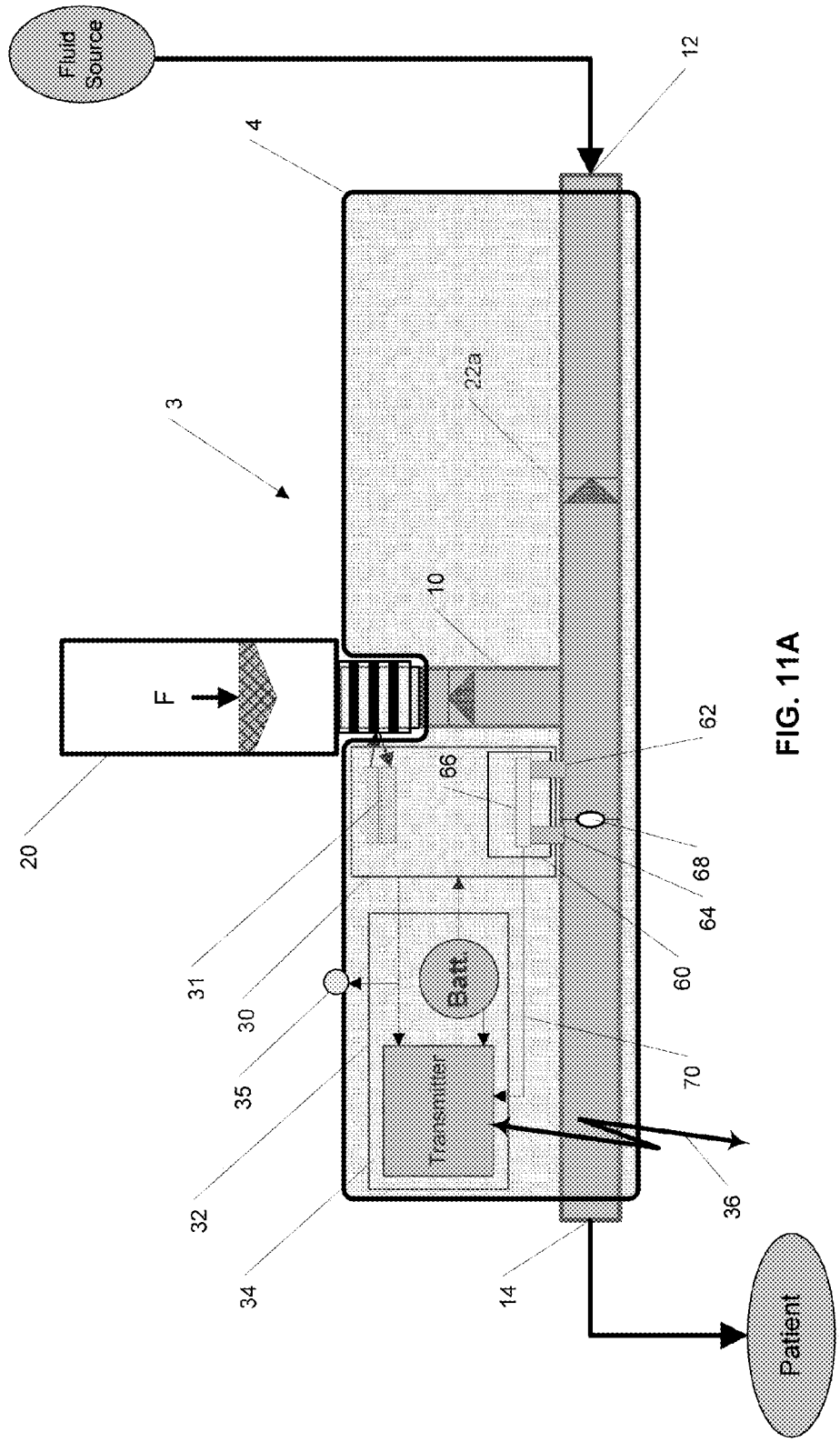
FIG. 11A is a diagram illustrating a medication injection site with a fluid flow measurement sensor on a first fluid channel.
Figure 11B:
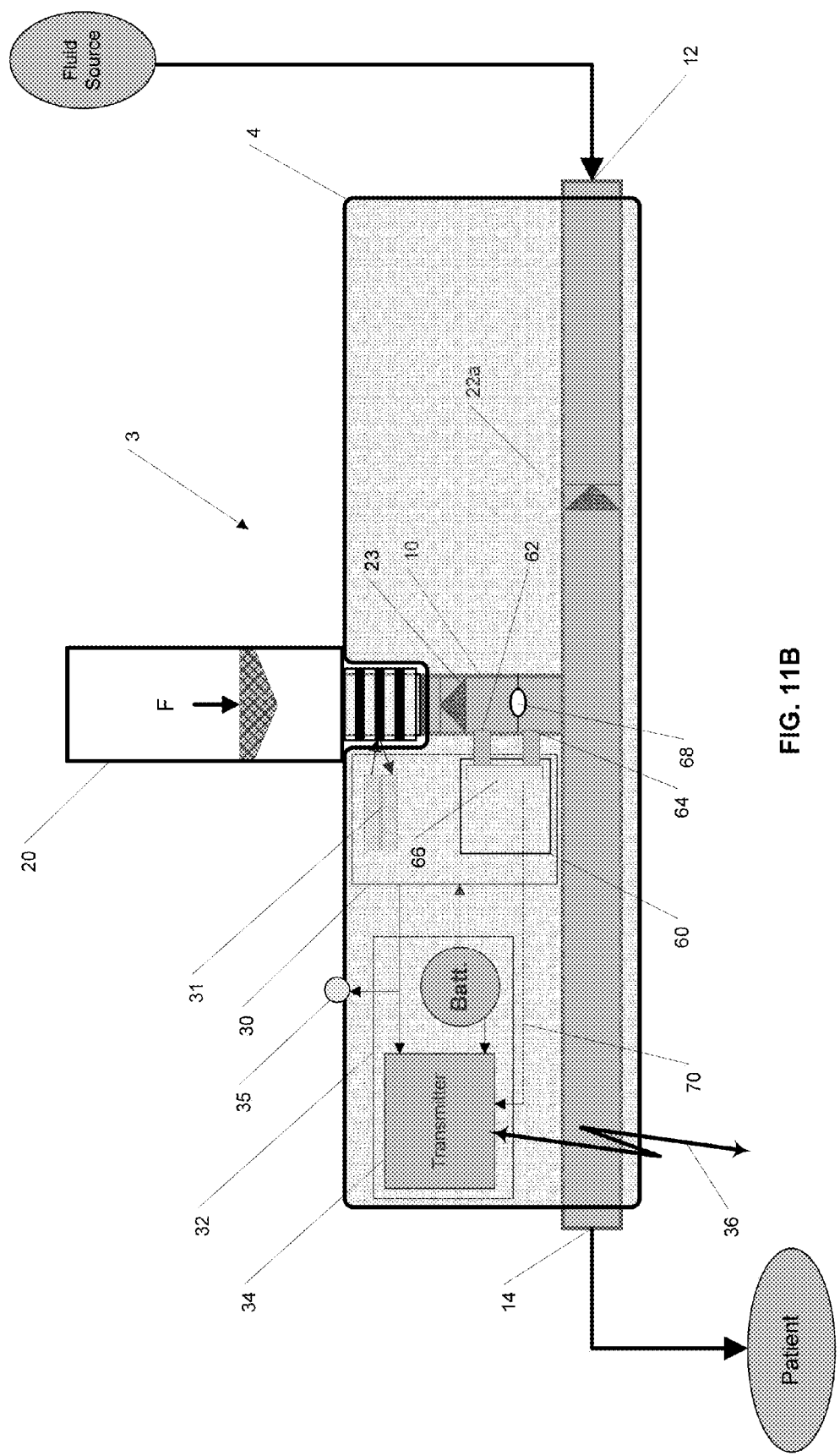
FIG. 11B is a diagram illustrating a medication injection site with a fluid flow measurement sensor on a second fluid channel.

FIGS. 11A and 11B depict a medication injection site 3 incorporating fluid flow sensor 60. The fluid flow sensor 60 can be a pressure measurement sensor with differential pressure inlets 62 and 64 that are fluidically connected to first fluid channel 8. Pressure transducer 66 can provide a differential pressure signal 70. When medication container 20 delivers fluid to the second fluid channel 10 there is a sudden increase in differential pressure signal 70 due to the fluid flow through orifice 68. This change in differential pressure indicates fluid delivery from medication port 13 is occurring. The value of differential pressure signal 70 can be provided to transmitter 34 and subsequently transmitted to receiver 42 as shown in FIG. 5. Pressure signal 70 can be sent to message decoder & display driver 46. Micro-computer 47 can contain algorithms to calculate fluid volume delivered based on the differential pressure. When the volume delivered equals the original volume in container 20 the end of medication delivery is logged. Knowing differential pressure, time, cross-sectional area of orifice 68 and cross-sectional area of first fluid channel 8 enables calculation of fluid volume delivered.

A variation of the medication injection site 3 system of FIG. 5 is shown in FIG. 11B and depicts a construction with the pressure transducer 66 positioned on second fluid channel 10 instead of on first fluid channel 8. Fluid inlets 62 and 64 can be located down stream or upstream of check valve 23. In this configuration, orifice 68 is located in second fluid channel 10 between inlets 62 and 64. Volume delivered is calculated in the same way as above using algorithms in micro-computer 47.

In other constructions, the fluid flow sensor 60 can include a single channel pressure transducer 66. In this variation, volume can be calculated as the integral of the pressure increase over time.

Figure 12:
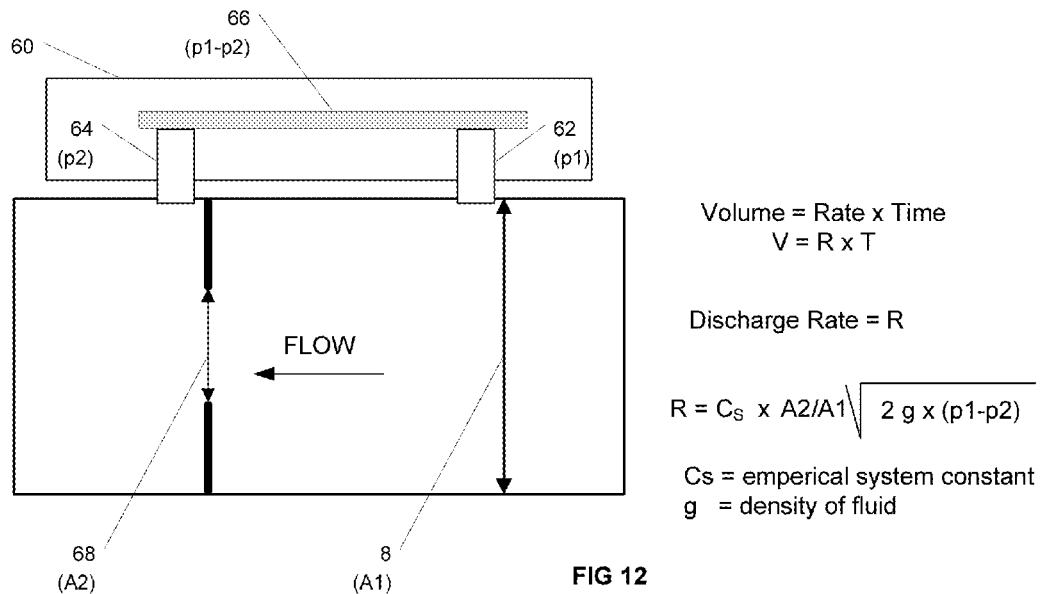
FIG. 12 is a diagram illustrating a flow measurement calculation method described for use with a medication injection site as in FIGS. 11A and 11B.

FIG. 12 depicts a detailed view of the pressure measurement components 62, 64 and 66 and orifice 68. Calculation of volume can be based upon the Bernoulli Equation and Volume=Rate×Time. The discharge rate R is calculated using the formula shown in FIG. 12 to the right where $C_s$ is an empirically derived constant for calibrating the system, A2/A1 is the ratio of the areas of orifice 68 (A2), first fluid channel 8 (A1) and "g" is the fluid density. The differential pressure 66 can be the pressure difference between inlet 62 (p1) and inlet 64 (p2). It can be assumed that density "g" of the fluid in medication container 20 is that of water. However, other fluids with other densities can be used and calculations adjusted accordingly. Volume calculation can be completed within circuit 60 before wireless transmission or circuit 44 (not shown) after wireless transmission.

In some variations, fluid delivery sensor 60 can be used to directly sense fluid flow. Such a fluid delivery sensor 60 can based upon one of a paddle wheel flow meter, a turbine flow meter, a thermal flow meter, an ultrasonic flow meter, a coriolis type flow meter, etc.

Figure 13A:
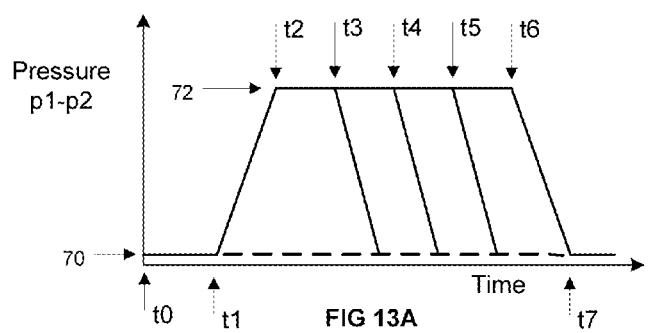
FIG. 13A is a diagram illustrating a first pressure-time graph for a flow measurement calculation method as in FIG. 12.
Figure 13B:
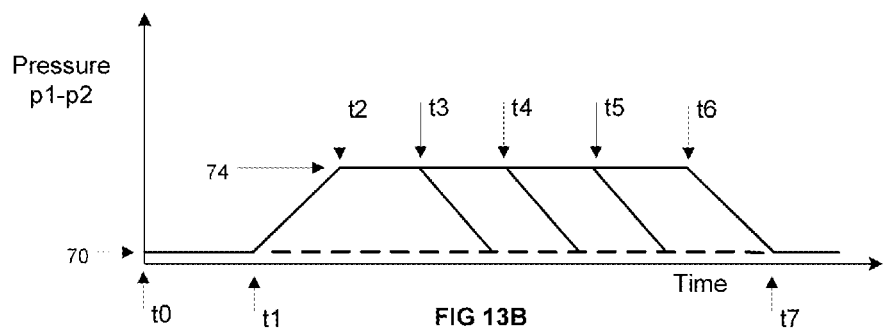
FIG. 13B is a diagram illustrating a second pressure-time graph for a flow measurement calculation method as in FIG. 12.

FIGS. 13A and 13B depict differential pressure-time graphs at various points in the operation of system shown in FIGS. 11A and 11B. FIG. 13A depicts a normal pressure time graph. Initially at time t0, pressure is at level 70 with no force applied to the medication container 20. At time t2 when the user increases force F by pressing on the plunger rod of a syringe or the medication container 20 of a reverse syringe, differential pressure increases from 70 to 72 at time t2 indicating user activity. This higher pressure 72 is sustained over time from t2 to t6 when the pressure returns to level 70 at time t7 when the medication administration is completed. The volume calculated confirms that the medication has been delivered. If the pressure is only maintained from t2 to t3 then an incomplete volume has been delivered. Various time points t3, t4, t5 and t6 are indicative of 25%, 50%, 75% or 100% volume delivered respectively. The volume calculation can be displayed to the user providing feedback on volume delivered and time stamp logged as a partial dose of medication.

FIG. 13B depicts a different pressure-time graph where the pressure is lower, indicative of slower delivery of medication. At time t1 the initial pressure 70 increases to level 74 which is less than pressure level 72 in FIG. 13A. The pressure is maintained for a longer period of time thru t3, t4, t5, and t6 where the pressure then decreases back to level 70 at time t7. Similarly as shown in FIG. 13A, if pressure is not sustained but instead drops down prematurely at t3, t4 or t5 an incomplete volume is calculated. There can be a number of other combinations of times and differential pressures used in calculating volume.

Figure 14A:
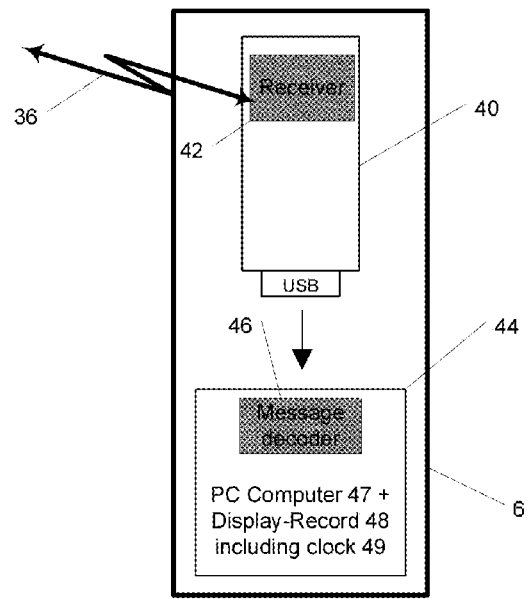
FIG. 14A is a diagram illustrating a data collection system with a wireless data receiver and removable memory.
Figure 14B:
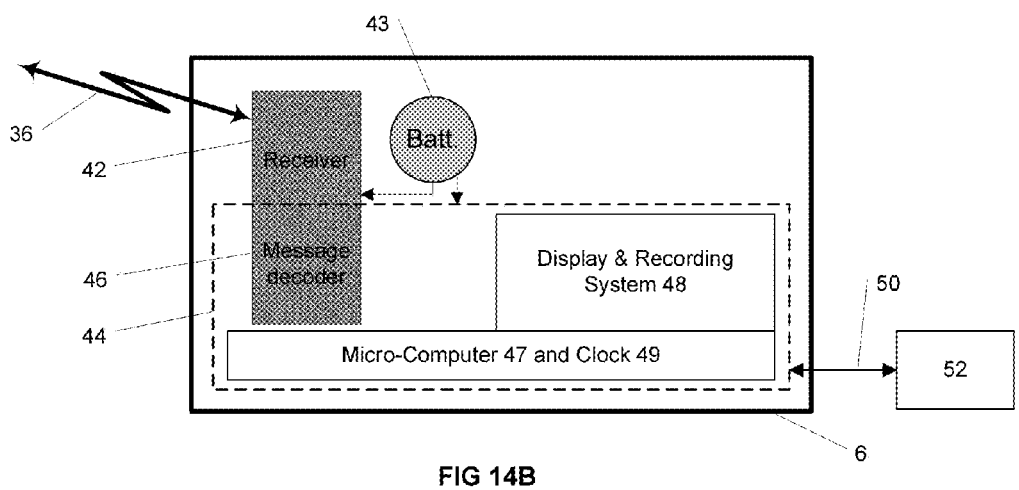
FIG. 14B is a diagram illustrating a data collection system with a wireless data receiver, a display, and a recording system.

FIGS. 14A and 14B depict two variations of data collection system 6. Display and recording system 48 can include any combination of hardware and software to receive signals from transmitter 34 and records the sequence of medication administrations. Receiver 42 can be a receiver only or a transceiver (i.e., a combined transmitter-receiver, etc.).

With reference to FIG. 14A, data collection system 6 can include a general purpose personal micro-computer 47 with a USB connection to receiver 42. In another embodiment shown in FIG. 14B, data collection system 6 can be stand alone and powered by a self-contained power source 43. FIG. 14A depicts a general purpose USB device with receiver 42 mounted in a USB housing with USB connection to a standard micro-computer 47 and message decoder 46. Information 36 received by receiver 42 is USB transferred to an external micro-computer 47. Software in message decoder 46 and micro-computer 47 can process information 36, add a time stamp from clock 49 and displays and logs the information via information display and recording system 48. Display, recording and logging function software is located in micro-computer 47. Micro-computer 47 can provide information 50 to a medical information system 52 as shown in FIG. 5.

FIG. 14B depicts a more integrated, self-contained and dedicated data collection system 6. Receiver 42, message decoder 46, micro-computer 47, display and recording system 48, clock 49 and micro-computer 47 are combined into one module. Receiver circuit 42, message decoder 46 and display and recording system 48 can be operated by micro-computer 47. A self-contained power source 43 provides energy for mobile operation.

Information circuit 44 can include or otherwise use software to provide the data collection system functions. These functions can be consolidated within a discrete data collection and record keeping device or distributed across a medical information system or a combination of both. When data collection system 6 is not functional or energized or when a patient is transferred from one data collection system 6 to a second data collection 6 memory 38 provides a history of medication administration data as discussed above. In this case second data collection system 6 can receive a medication administration data history and timer counts between subsequent medication administrations. The software automatically associates the medication administrations with real time from clock 49. Display recording system 48 is configured to process the previously recorded data, time stamp, log and display the information for the user.

Additionally, the software within data collection system 6 can include stored information in support of a series of medication administrations based upon an acute care protocol or various medication administrations unrelated to an acute care protocol. Thus, the software can display stored messages based upon medication injections in support of acute care protocol providing health care providers guidance in the conduct of the protocol. The software within data collection system 6 can include a set of rules to cause alerts and or alarms to occur (directly by the data collection system 6 or by transmitting data to another system, etc.) to inform the healthcare provider with information about the protocol. The protocol can be a non-acute care protocol wherein the care management of a patient is recorded and verified for proper drug, dose, time of administration. Other healthcare protocols can be envisioned that require monitoring, verification and documentation of medication administration.

Care protocols, such as acute care protocols, can be updated periodically, annually, or when studies indicate a need for updating. Information circuit 44 can be configured to receive updated information 50 from a medical information system 52 that is indicative of the most recent acute care protocols or protocol updates. Information circuit 44 software is in turn configured to update itself pursuant to the update information. The updated information can improve any operational aspect of the software.

While the discussion above describes an arrangement in which "raw" data is transmitted from the medication injection site 3 to the data collection system 6 so that micro-computer 47 can process such raw data to identify traits such as patient identification (e.g., serial number or other unique identifier of medication injection site 3), medication container contents, volume, expiration date, and/or pressure or volume information, and/or other complementary information, it will be appreciated that one or more of such traits can be determined by the medication injection site 3. For example, memory 38 may contain mapping data which associates raw data generated by identification sensor 18 into one or more of: an identification of the patient or the medication injection site 3 (e.g., serial number, etc.), contents of medication container 20, volume of medication container 20, or expiration date of the contents of medication container 20. This information can then be transmitted by transmitter 34 to data collection system 6.

Figure 15:
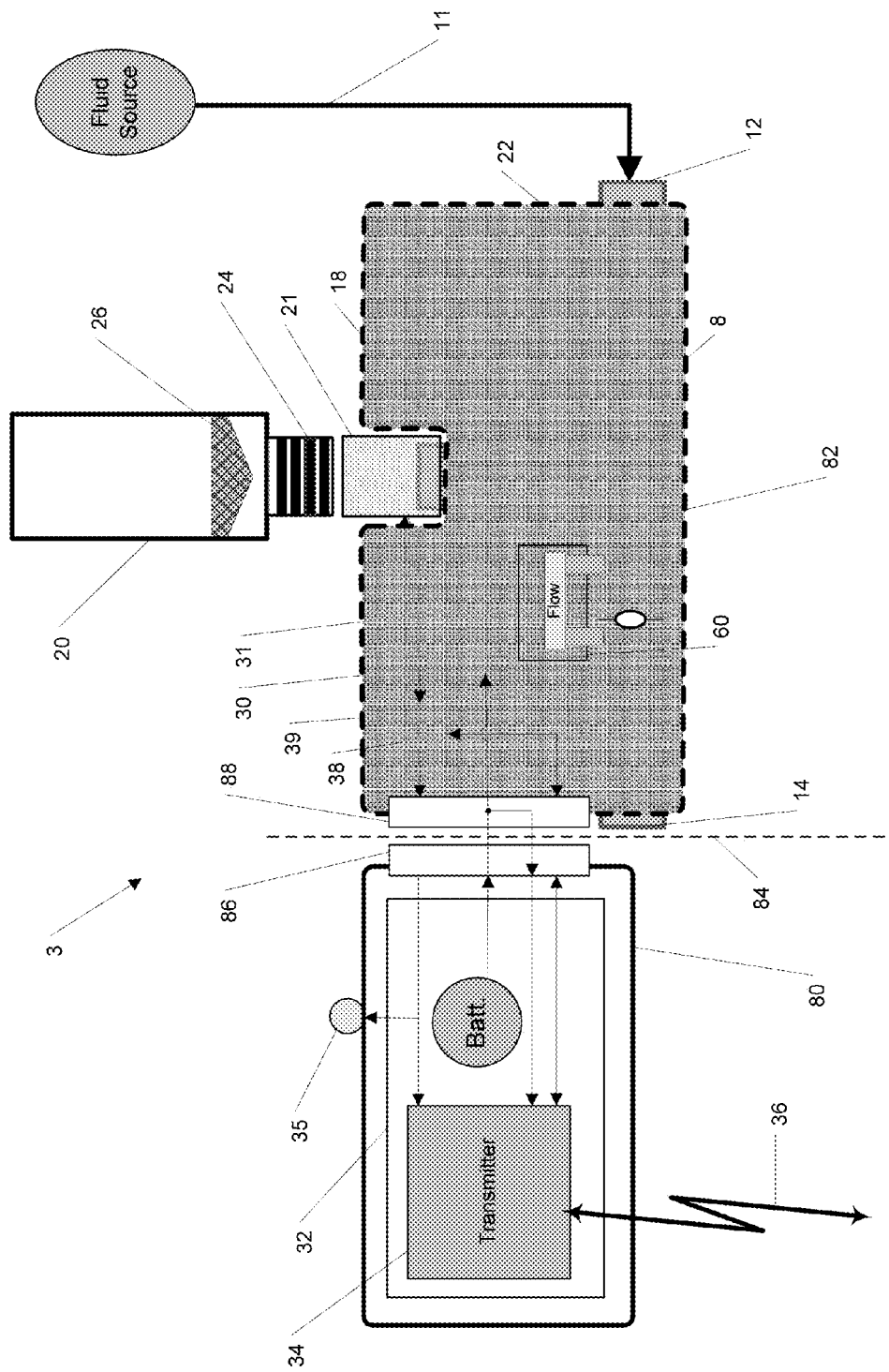
FIG. 15A is a diagram illustrating a first variation of medication injection site that includes a disposable sub-housing and a reusable sub-housing.
FIG. 15B is a diagram illustrating a second medication injection site that includes a disposable sub-housing and a reusable sub-housing.
FIG. 15C is a diagram illustrating a third medication injection site that includes a disposable sub-housing and a reusable sub-housing.
FIG. 15D is a diagram illustrating a fourth medication injection site that includes a disposable sub-housing and a reusable sub-housing.
Figure 15:
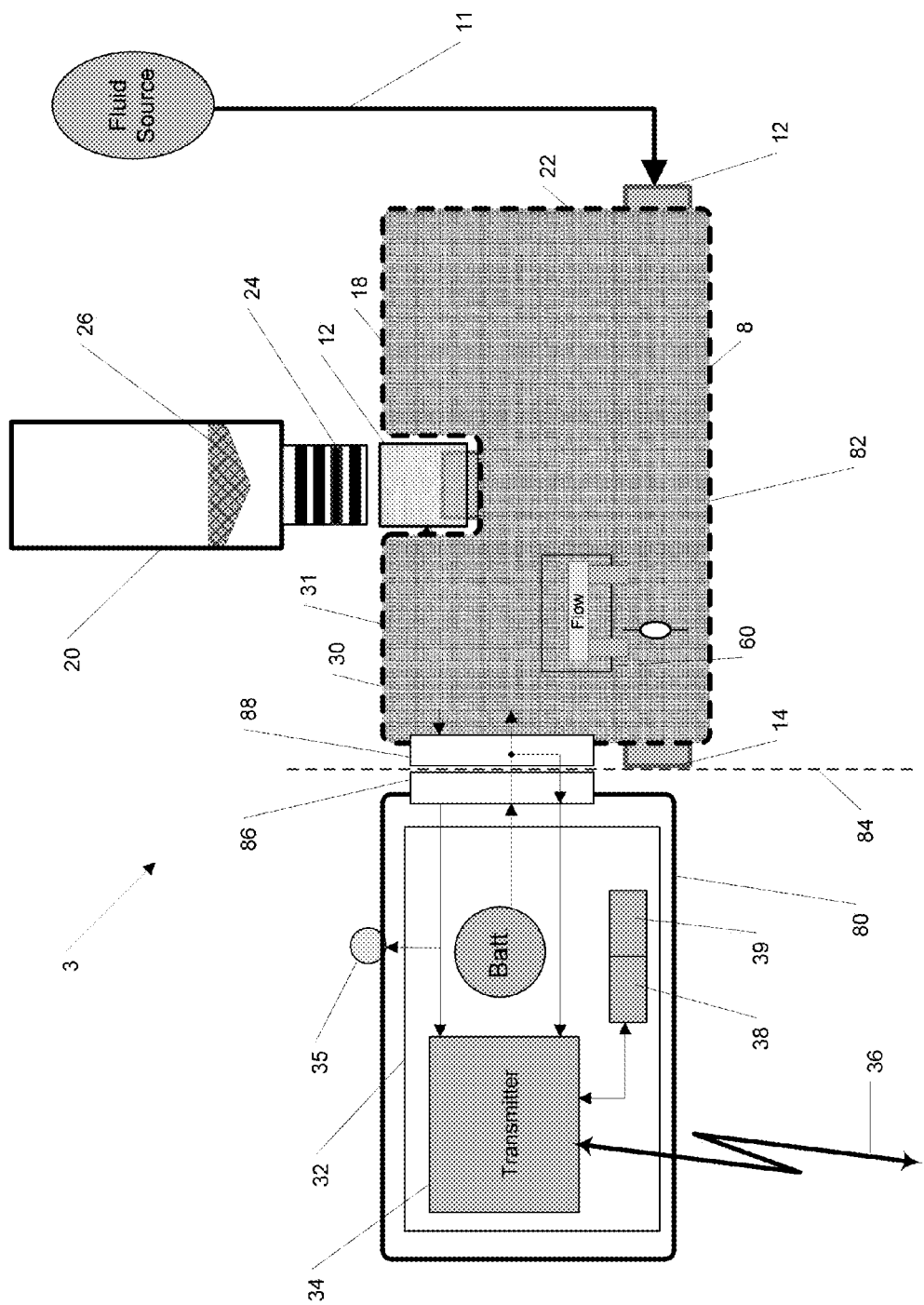
Figure 15:
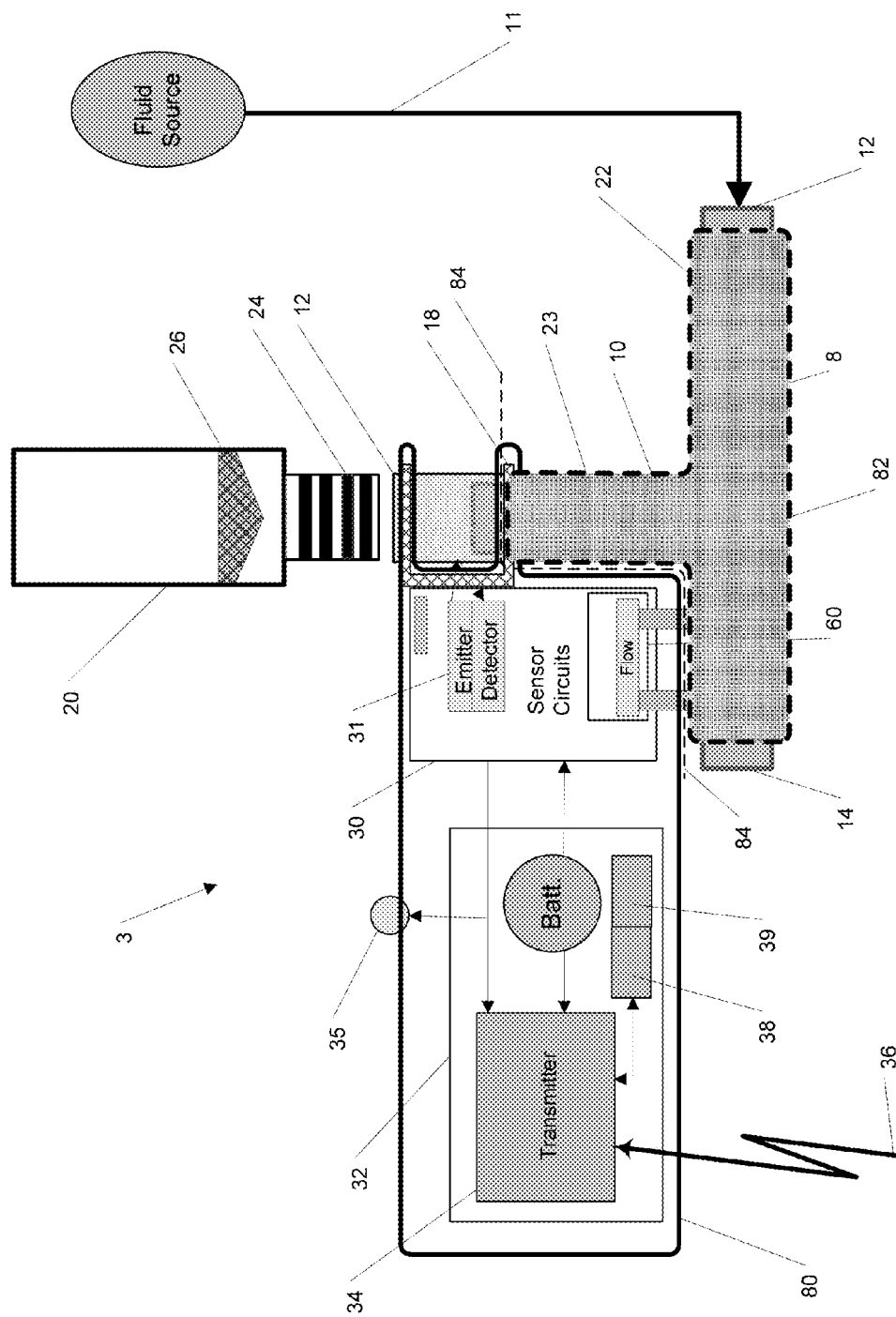
Figure 15D:
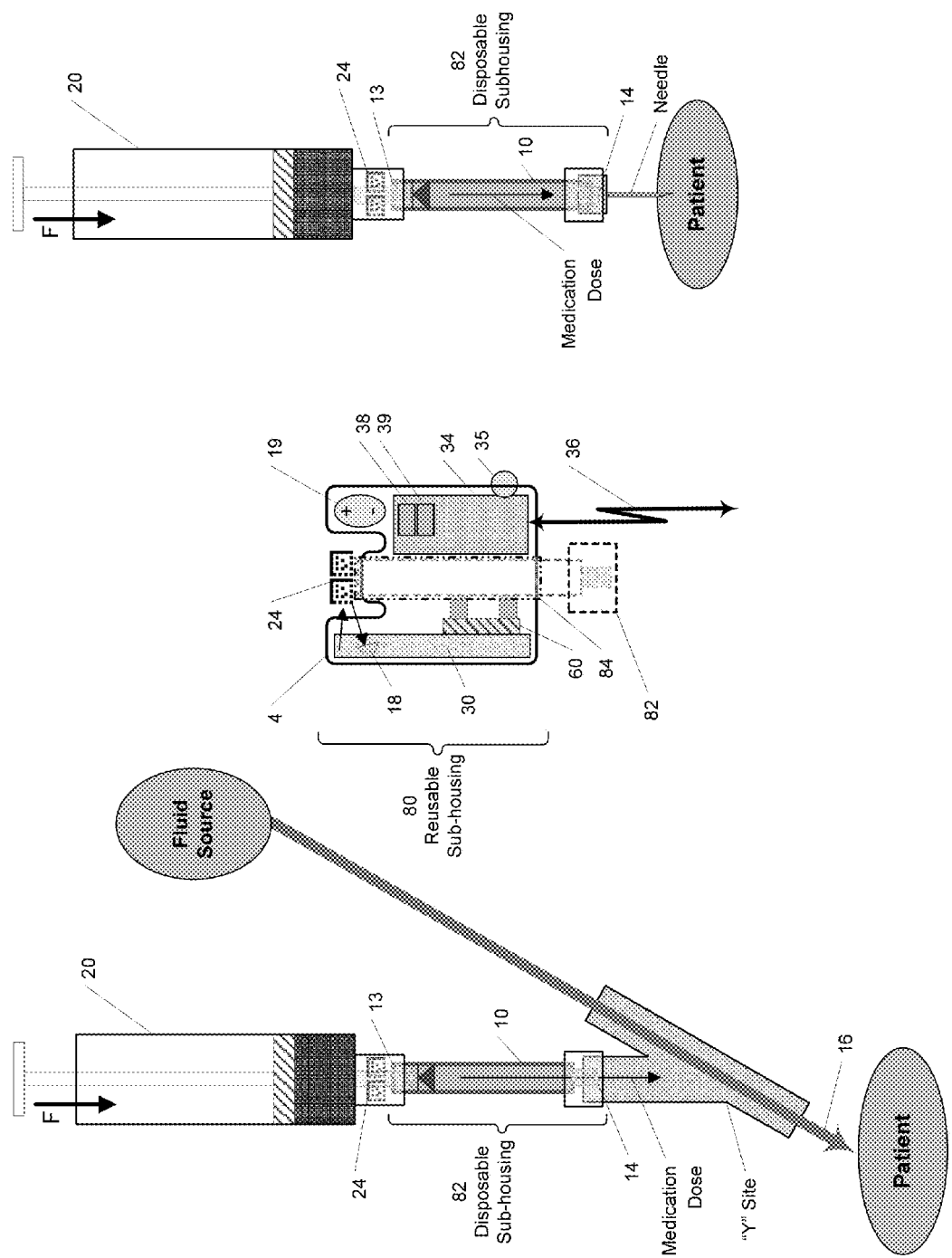

FIGS. 15A, 15 B and 15C depict housing 4 as shown in FIG. 3A separated into reusable sub-housing 80 and disposable sub-housing 82. FIG. 15D depicts housing 4 as shown in FIGS. 2C and 2D separated into reusable sub-housing 80 and disposable sub-housing 82. Various constructions can be utilized that distribute elements of medication injection port 3 either to reusable sub-housing 80 or to disposable sub-housing 82. Four variations are described below, however, other implementations can be adopted based on considerations such as overall size, weight, per-patient costs, etc. When used, reusable sub-housing 80 is connected to disposable sub-housing 82 through interface 84. When connected, medication injection site 3 becomes functional by providing power from power source 19 ("Batt"). When the power source is contained in reusable sub-housing 80 a charging element (not shown) can be configured to recharge the power source between uses. When the power source is self-contained within disposable housing 4 no recharging is needed (see FIGS. 3A, 4A and 5).

FIG. 15A depicts a first sub-housing implementation in which reusable sub-housing 80 can include one or more of: transmitter 34, battery, indicator 35 and connector 86. In this variation, disposable sub-housing 82 can include one or more of: memory 38, timer 39, sensor circuit 30, emitter/detector 31, flow sensor 60, identification sensor 18, first fluid channel 8, second fluid channel 10, check valve 22, check valve 23 and connector 88. Interface 84 can be formed by mating connector 86 with connector 88 and can be one or more of an electrical contact, a mechanical contact, an optical coupling, an electrical contact coupling or a magnetic coupling.

FIG. 15B depicts a second sub-housing implementation in which reusable sub-housing 80 can include one or more of: transmitter 34, battery, indicator 35, memory 38, timer 39 and connector 86. Disposable sub-housing 82 can include one or more of: sensor circuit 30, emitter/detector 31, flow sensor 60, identification sensor 18, first fluid channel 8, second fluid channel 10, check valve 22, check valve 23 and connector 88. Interface 84 can be formed by mating connector 86 with connector 88 and can be one or more of an electrical contact, a mechanical contact, an optical coupling, an electrical contact coupling or a magnetic coupling.

FIG. 15C depicts a third sub-housing implementation in which reusable sub-housing 80 can include one or more of: transmitter 34, battery, indicator 35, memory 38, timer 39, sensor circuit 30, emitter/detector 31, flow sensor 60 and identification sensor 18. Disposable sub-housing 82 can include one or more of: first fluid channel 8, second fluid channel 10, check valve 22, and check valve 23. Interface 84 can be formed by one or more of a hydraulic coupling, a mechanical coupling, an optical coupling, an electrical contact coupling or a magnetic coupling.

FIG. 15D depicts a fourth sub-housing implementation configured for direct medication administration as shown in FIGS. 2C and 2D. Reusable sub-housing 80 is shown in the center and can include one or more of: transmitter 34, a processor, battery 19, indicator 35, memory 38, timer 39, sensor circuit 30, emitter/detector 31, flow sensor 60 and identification sensor 18. Disposable sub-housing 82 shown to the left and to the right can include one or more of: second fluid channel 10 and check valve 23. The interface 84 between reusable sub-housing 80 and disposable sub-housing 82 can be formed by one or more of a hydraulic coupling, a mechanical coupling, an optical coupling, an electrical contact coupling or a magnetic coupling.

Figure 16A:
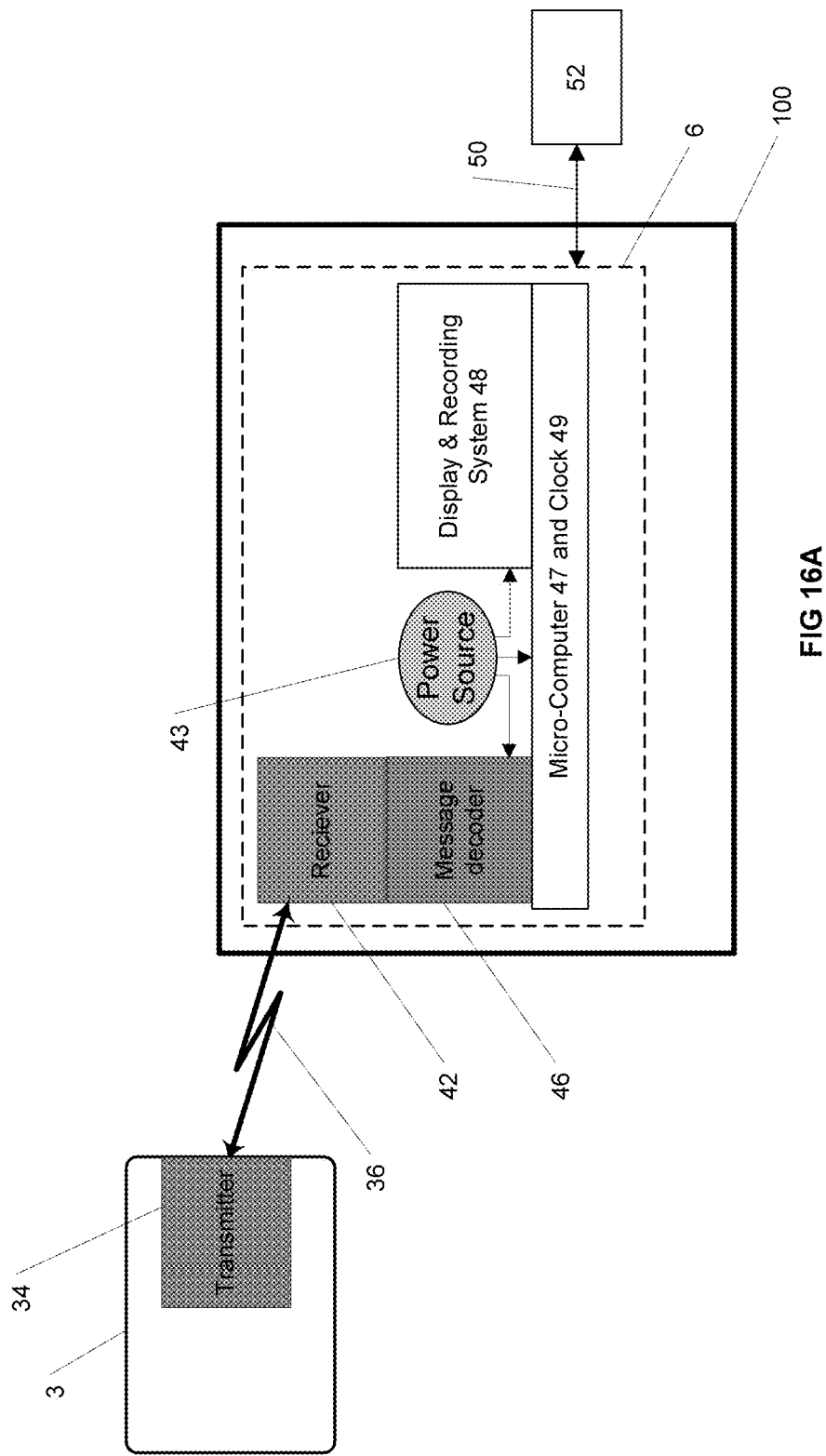
FIG. 16A is a diagram illustrating a secondary medical device configured to receive wireless information from a medication injection site.
Figure 16B:
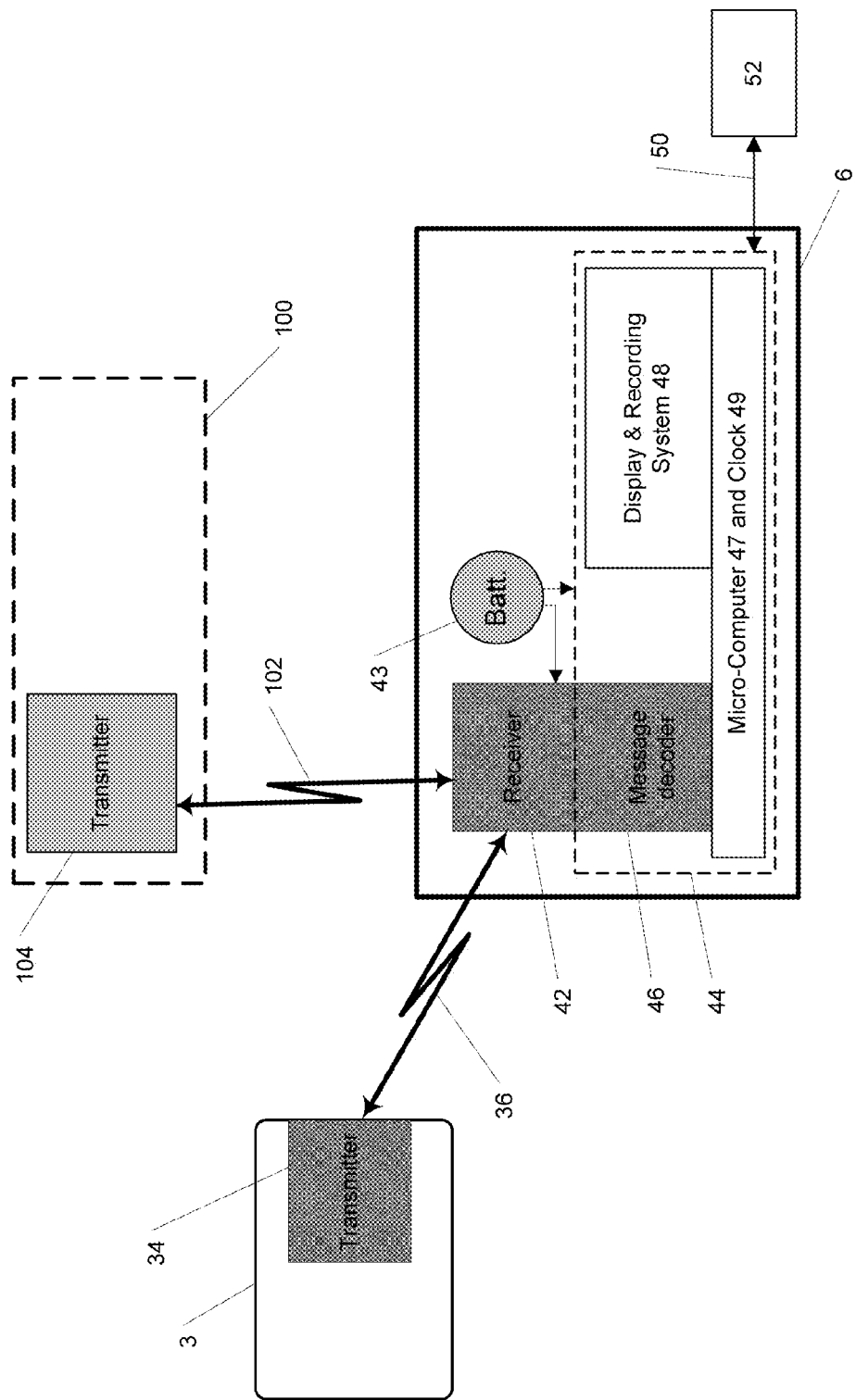
FIG. 16B is a diagram illustrating a data collection system to receive wireless information from a medication site and from a secondary medical device.
Figure 16C:
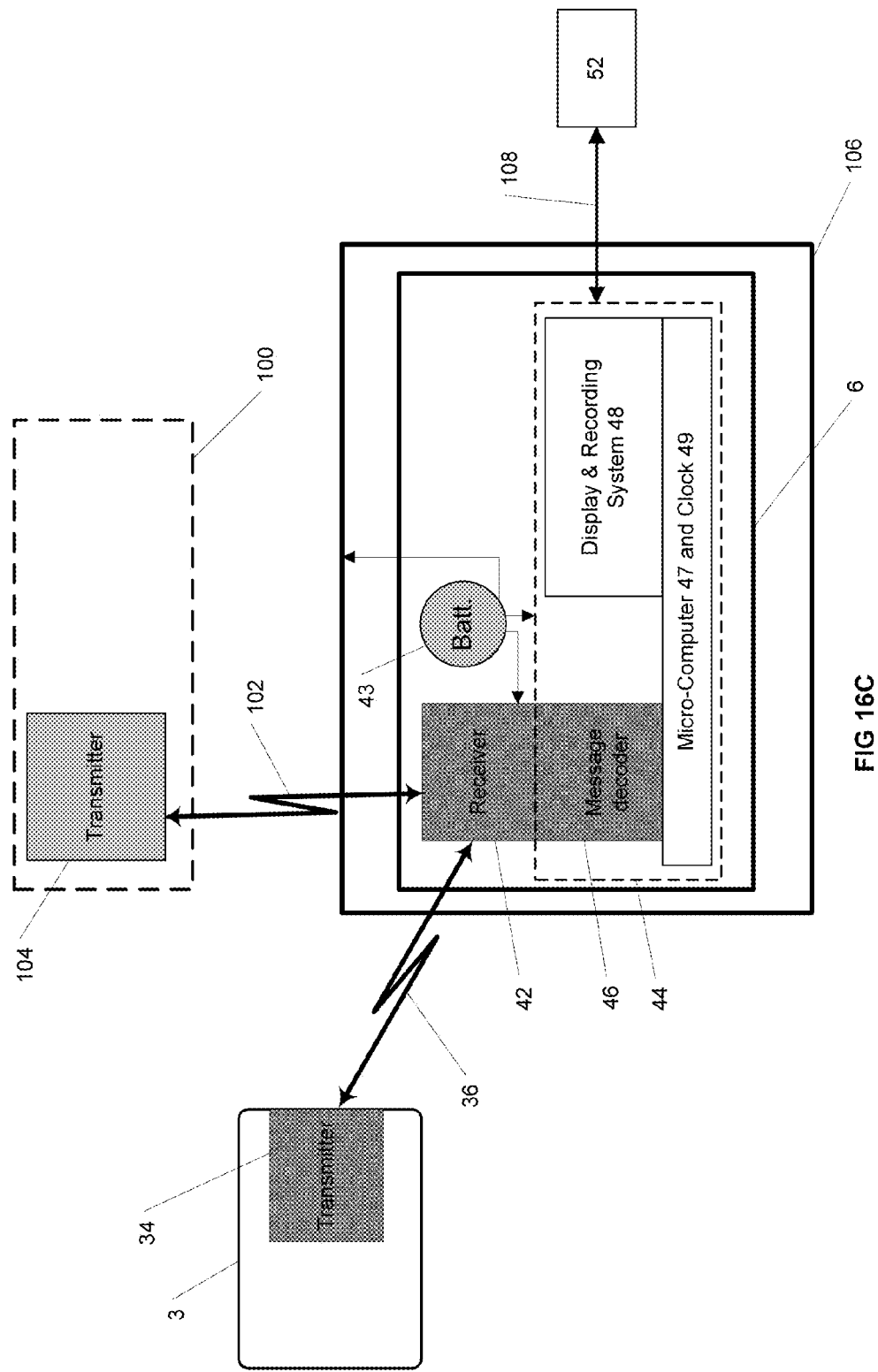
FIG. 16C is a diagram illustrating a data collection system configured as a cellular phone to receive wireless information from a medication injection site and/or a secondary medical device.

FIGS. 16A, 16B and 16C depict three additional variations of data collection system 6. FIG. 16A depicts a variation of a data collection system in which data collection 6 is coupled to or forms part of a secondary medical device 100 such as an EKG monitor, an EEG monitor, a blood pressure monitor, a defibrillator, a pulse oximeter, an $ETCO_2$ monitor, bar code medication administration (BCMA) system, an IV pump, or any other physical device and/or system used directly or indirectly for the delivery of patient care. Data collection system 6 can receive medication administration data or other information 36 collected by medication injection port 3 by receiver 42. Information 36 is processed through message decoder 46 to micro-computer 47. The software automatically associates the time stamped medication administrations or other information received with real time using clock 49. Display recording system 48 can process the previously recorded data, time stamp, log and display the information for the user. The secondary medical device 100 can provide information 50 such that it transfers medication administration data or other information 36 from recording system 48 to medical information system 52. Medical information system 52 can be a single system or network of integrated systems including but not limited to Admission, Discharge and Transfer Systems (ADT); Pharmacy Information Systems (PIS); OR Information Systems (ORIS); Electronic Medical Record Systems (EMR); Patient Scheduling Systems (PSS); Electronic Medication Administration Systems (eMAR); and the like. Information 50 can also include data transmitted from medical information system 52 to secondary medical device 100 applicable to the processing, routing and/or association of information 36 received from medication injection port 3.

FIG. 16B depicts another variation of a data collection system 6 that can wirelessly receive information 102 from a secondary medical device 100 such as an EKG monitor, an EEG monitor, a blood pressure monitor, a defibrillator, a pulse oximeter, an $ETCO_2$ monitor, a BCMA system, an IV pump, or other physical device and/or system used directly or indirectly for the delivery of patient care. In this configuration, transmitter 104 within medical device 100 transmits information 102 to receiver 42 within data collection system 6. Information 102 is processed through message decoder 46 to micro-computer 47 and is time stamped by clock 49. This information is integrated in time with medication administration or other information 36 and is displayed and logged by recording system 48. The user can be provided with integrated data from medication injection site 3 and medical device 100.

FIG. 16C depicts another variation of a data collection system 6 that can wirelessly receive information 36 from medication site 3 and a secondary medical device 100 such as an EKG monitor, an EEG monitor, a blood pressure monitor, a defibrillator, a pulse oximeter, an $ETCO_2$ monitor, a BCMA system, an IV pump, or other physical device and/or system used directly or indirectly for the delivery of patient care. In this configuration, transmitter 34 within medication site 3 transmits medication administration information 36 to receiver 42 within data collection system 6. Data collection system 6 can be coupled to or form part of a cellular phone 106. Additionally, data collection system 6 within cellular phone 106 can wirelessly receive information 102 from a secondary medical device 100 such as an EKG monitor, an EEG monitor, a blood pressure monitor, a defibrillator, a pulse oximeter, an $ETCO_2$ monitor, an IV pump, or other physical device and/or system used directly or indirectly for the delivery of patient care. Information 102 is processed through message decoder 46 to micro-computer 47 and is time stamped by clock 49. This information 102 is integrated in time with medication administration or other information 36 and is displayed and logged by recording system 48. The user can be provided with integrated data from medication injection site 3 and medical device 100. The cellular phone 106 can provide information 108 such that it transfers medication administration or other information 36 and medical device information 102 from recording system 48 to medical information system 52. Information 108 can also include data transmitted from medical information system 52 to cellular phone 106 applicable to the processing, routing and/or association of information 36 received from medication injection port 3 and/or information 102 received from medical device 100.

Figure 17:
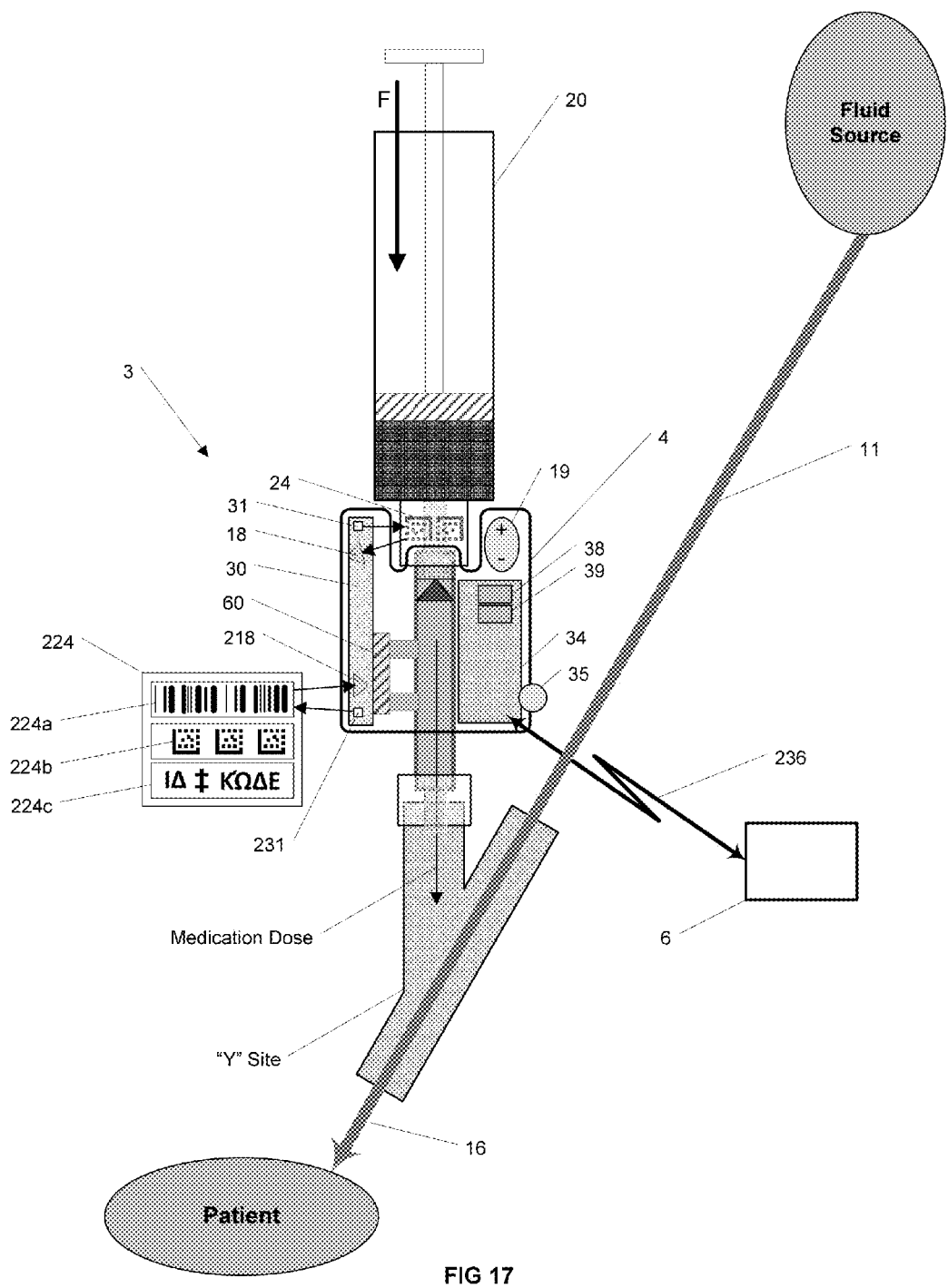
FIG. 17 is a diagram illustrating a second identification sensor to receive information from a second information source.

FIG. 17 depicts a second information source 224 and a second identification sensor 218. The second information source 224 can provide complementary information associated with patient treatment, medication injections and/or use of medication port 3 on a particular patient or as part of a particular clinical workflow activity. The second information source 224 can provide information relevant to patient treatment and/or clinician workflow that is otherwise independent from information read by information sensor 18. Identification sensor 218 can be used: 1.) in conjunction with identification sensor 18 to read data from information source 224 which is complimentary to information source 36; 2.) independent of identification sensor 18 to read data from information source 224 which is disparate from information source 24 but related to the same patient and/or clinical workflow; or 3.) instead of identification sensor 18, in which case identification sensor 218 functions as the primary identification sensor and information source 224 serves as the primary information source.

The second identification source 224 can contain optical (1 dimensional barcode, 2 dimensional barcode, symbolic information, image or picture), magnetic (magnetic strip on an identification card/badge/ID tag), an NFC tag, biometric and/or RFID encoded or non-encoded information. The second information source 224 can be illuminated by an optical emitter 231 (LED). Information source 224 can take the form of a one dimensional barcode 224a, a two dimensional barcode 224b, a symbolic code 224c ("IΔ‡KΩΔE"=ID Code) or other coded information. The information read by the second identification sensor 218 can also take the form of non-encoded information such as a photograph, video, or biometric characteristic (fingerprint, heart rate, etc.). The information can be indicative of one or more of the following:

a patient, a patient demographic, a patient medical record (picture, video, biometric parameter patient ID, medical record number, weight, medical and/or medication history, present conditions, height, sex, age, eye color, allergies and/or other contraindications, Broselow color, etc.), a patient sample (patient ID, blood sample, urine sample, tissue sample, stool sample, other body fluid sample, etc.), a medical device (device ID, IV pump, EKG monitor, defibrillator, pulse oximeter, blood pressure monitor, etc.), a patient input and/or output (medication, blood, urine, fluid, food, etc.), a diagnostic test and/or treatment result (lab values, radiological images and/or information, vital sign trends, EKG strip, clinical report, etc.), a caregiver (picture, video, fingerprint, ID code/password, employee ID, name, affiliation, clinical role, responsibility for patient, decision-making authority etc), a family member and/or companion (picture, video, fingerprint, ID number, affiliation, breast milk, organ donation, contact information, Advance Healthcare/Medical Directive authority and/or instructions, etc), a pharmacy record (prescription number, patient ID, formulation, expiration date, administration instructions and/or precautions, contraindications, medication reconciliation information, pharmacy ID, preparer ID, etc.)

a physician's order (e.g., medication administration orders, lab orders, diagnostic testing orders, radiological orders, treatment and/or therapy orders etc.), an environmental factor (room number, temperature, time, care transition status, time of admission, time of last bed sheet change, etc).

In some variations, identification sensor 218 can generate such information when second information source 224 is coupled or is in proximate location to second identification sensor 218. Identification sensor 218 can be any one or more of: an optical sensor, a mechanical sensor, an electrical sensor, a magnetic sensor, an NFC sensor, an RFID sensor, a proximity sensor. A transmitter 34 can be disposed within housing 4 and in communication with or coupled to identification sensor 218 to wirelessly transmit the information 236 generated by the identification sensor 218 to the remote data collection system 6. The signal from identification sensor 218 can be processed and readied for transmission by sensor circuit 30. Sensor circuit 30 processing can include but is not limited to decoding, encoding, pattern recognition (e.g. conversion of image date to text), filtering, image enhancement, analog to digital conversion, or mapping to secondary data via a lookup table. A self-contained power source 19 (e.g., battery or battery array, etc.) can be disposed within housing 4 to provide power for one or more of identification sensor 18, identification sensor 218, fluid delivery sensor 60, sensor circuit 30, transmitter 34 and indicator 35.

Figure 18:
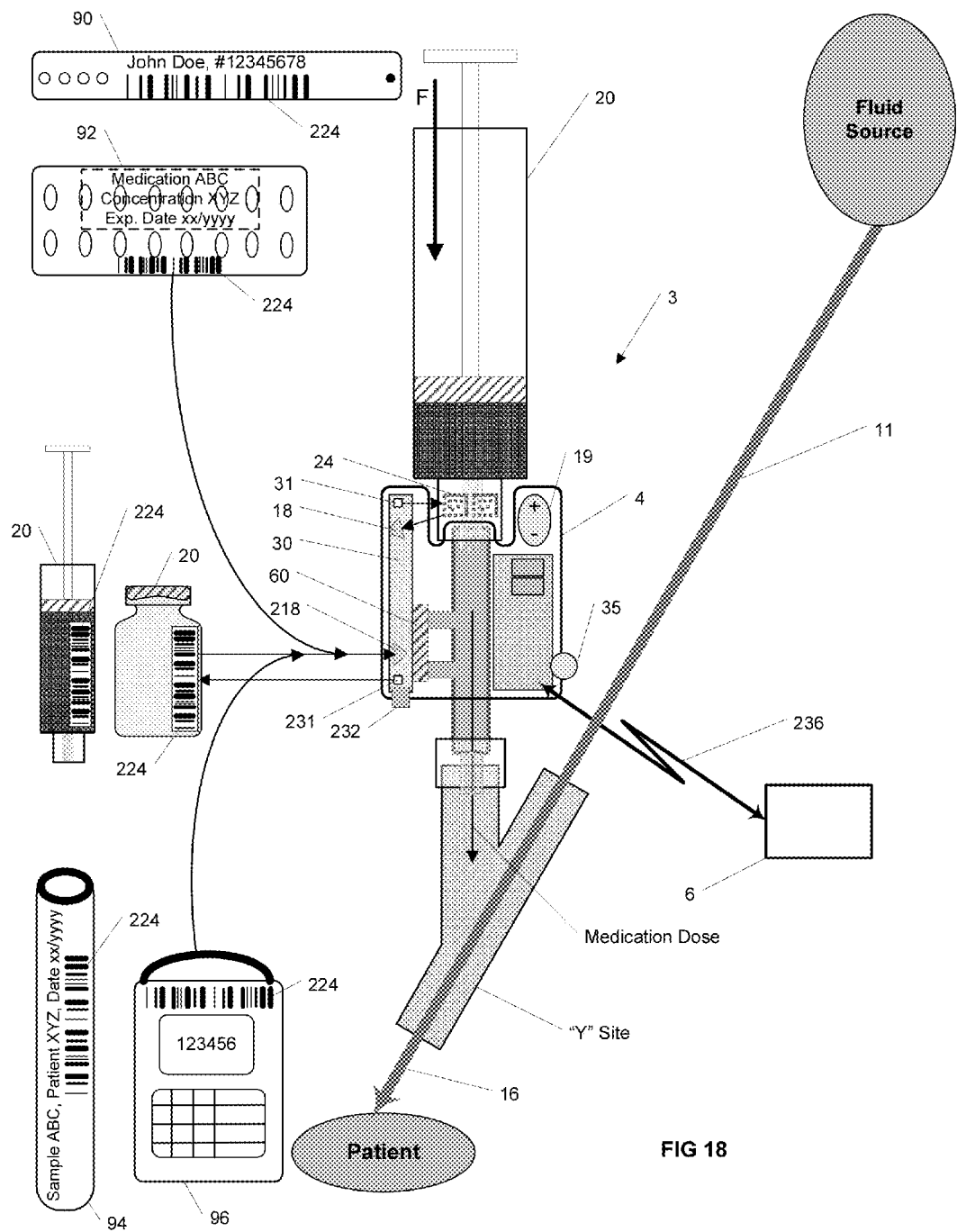
FIG. 18 depicts use of a second identification sensor to detect complementary information from a medication information source.

FIG. 18 depicts use of identification sensor 218 to detect information from any applicable external information source 224. Information source 224 can reside on or be integrated into medication containers 20 (syringes, vials as shown) or other medication containers (fluid bags, ampoules, blood bags, IV tubing sets, medication patches, auto-injection devices, among others not shown). Information read by identification sensor 218 from containers can include but is not limited to one or more of: type of medication, concentration of medication, volume of medication, expiration date of medication, or the NDC or RXnorm code for a medication. An activation switch 232 can manually activate the emitter 231 and information sensor 218 to detect information source 224. Identification sensor 218 can alternatively detect information from a non-medication information source 224 as depicted in FIG. 18. As shown in FIG. 18, information can include a patient wrist band 90, an oral solid package 92, a patient sample container 94, and a medical device 96. FIG. 18. provides illustrative examples of items which can be tagged with information source 224 but is not meant to be limiting since the information read by identification sensor 218 can include or be indicative of any one of or a combination of the elements previously described. Information source 224 can be detected by information sensor 218, transmitted to data collection system 6, processed there for time stamping, can be associated with patient identification or other association factors, and further recorded in health system records. Processing of data received from information source 224 can be done completely by data collection system 6 or can be distributed across a chain of devices and/or systems in communication with data collection system 6 including medication injection site 3, medical device 100, cellular phone 106 and medical information system 52.

In one embodiment, for example, medication injection site 3 can serve as the front end of a barcode medication administration system (BCMA), where identification sensor 218 can be a camera that can be used by a clinician to first read a patient ID encoded in information source 224 on a patient wristband 90. The patient ID can be processed by data collection system 6 using a data set of patient demographic data received from the ADT subsystem of medical information system 52. The clinician can then use identification sensor 218 a second time to read a medication NDC number encoded in another information source 224 on a medication container 20 that can be a vial of medication. The NDC number can be processed by data collection system 6 to determine the medication type and concentration contained in the vial and can be verified against a medication administration order received from the PIS subsystem of medical information system 52 to ensure the contents of the vial are safe and appropriate for delivery to the patient whose patient ID was previously read. Once verified, the clinician can draw up the some or all of the contents of the vial into a syringe which can be fluidically coupled to medication port 13 and administered to the patient. During the fluid administration, fluid flow characterization sensor 60 can measure the actual volume or composition of medication delivered to the patient. Once fluid flow has stopped, data collection system 6, can use the concentration read from the vial to convert the measured fluid volume to dose administered; and that dose amount, the medication type read, and any other pertinent data is aggregated, time stamped, and can be sent by data collection system 106 to the eMAR subsystem of medical information system 52.

Using similar logic and workflow, identification sensor 218 of medication injection port 3 can be utilized for other positive patient identification (PPID) applications involving the collection, time stamping, association and recording of clinical items and/or activities related to a particular patient. Further examples of such PPID embodiments include applications where clinical samples and/or specimens are matched to a patient; breast milk is matched to both a mother and child; blood is matched to a patient; and medical devices are matched to a particular patient.

Identification sensor 218 can also be used for reading data into medication injection port 3 for use at a future time. For example, identification sensor 218 can be used to read and store patient identification and demographic information from information source 224 such that each time a medication is administered through medication injection port 3, the stored patient data is referenced and used for routing the resultant medication administration event data to the proper patient medical record. Similarly, identification sensor 218 can be used to read and store patient-specific medication allergy information from information source 224 such that each time a medication container 20 is coupled to injection site 13, the stored medication allergy information is referenced and used to determine whether or not the patient has an allergy to the medication that is about to be administered. Such programming and/or reference data can be used directly by medication injection port 3, or in combination with data collection system 106 and other devices and/or systems in direct or indirect communication with medication injection port 3.

Figure 19:
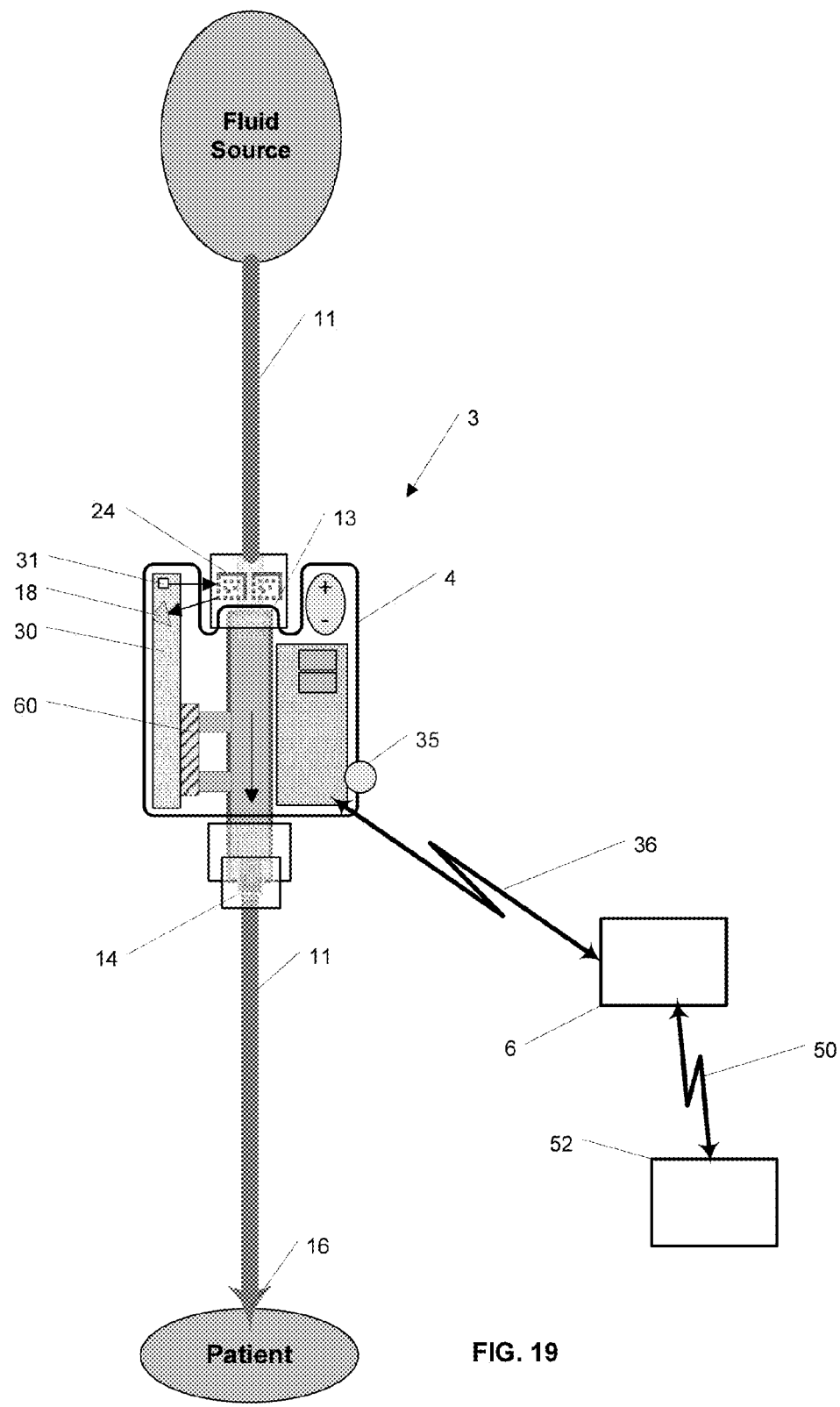
FIG. 19 is a diagram illustrating a fluid delivery tubing set connected to a medication injection site for continuous infusions to a patient; and Like reference symbols in the various drawings indicate like or similar elements.

FIG. 19 is a diagram illustrating a fluid delivery tubing set 11 connected to medication injection port 3 for continuous infusion to a patient. Tubing set 11 can be coupled to medication injection site 3 input 13 and output 14 can be connected to downstream tubing leading to a patient. A patient access device 16 (catheter, needle) can couples the tubing set 11 to the patient. Housing 4 can contain a fluid flow characterization sensor 60 (a flow volume and/or flow rate measurement, a composition sensor (not shown), a pressure sensor (not shown), an air in line sensor (not shown), a temperature sensor (not shown)) or other detectors and/or sensors. In use medication port 3 can monitor and/or measure fluid delivery characteristics in tubing set 11. Initially, and upon fluid coupling of tubing set 11 to medication port 3, information source 24 on the luer output coupling fitting of tubing set 11 is read by information sensor 18. This fluid source information 24 can be associated with a particular patient and/or procedure at the data collection system 6. When fluid is administered to the patient, fluid delivery sensor 60 can monitor and/or measure one or more of: fluid flow, fluid volume, fluid composition, air (absence of fluid), temperature, pressure. Additionally, data from the various sensors (flow volume, flow rate, fluid composition, pressure, temperature, air, other) can be transmitted 36 to data collection system 6. Data collection system 6 can provide various information 50 to medical information system 52, a secondary medical device 100 (not shown), a cellular phone 106 (not shown), a personal computing device (iPad or tablet computer for example, not shown), a home health care transmitter or computing device (not shown).

Aspects of the subject matter described herein can be embodied in systems, apparatus, kits (e.g., kits with the medication injection site being enclosed therein), methods, and/or articles depending on the desired configuration. In particular, aspects of the subject matter described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A medication delivery apparatus for use with a medication source comprising:
    a housing;
    a fluid conduit at least partially extending within the housing and configured to deliver medication from the medication source to a patient via a parenteral fluid administration pathway;
    a medication port extending from an external surface of the housing and configured to be coupled to a tubing set coupled to the medication source, the medication port being fluidically and directly coupled to the fluid conduit; and
    at least one first sensor disposed within the housing to generate information characterizing administration of the medication for processing by a remote data collection system;
    wherein the at least one first sensor includes an identification sensor and the tubing set includes an information source selected from a group consisting of: mechanically encoded information, magnetically encoded information, radio frequency readable information, or optically encoded information, wherein the identification sensor reads the information from the information source.

2. A medication delivery apparatus as in claim 1, further comprising: at least one second sensor disposed within the housing to generate complementary information for processing by the remote data collection system.

3. A medication delivery apparatus as in claim 2, wherein the complementary information comprises encoded information.

4. A medication delivery apparatus as in claim 3, wherein the remote data collection system associates the information generated by the at least one sensor and/or the complementary information generated by the at least one second sensor with one or more of: medication information, patient identification, patient weight, patient sex, patient age, patient BROSELOW color, pre-existing and/or current patient medical conditions, patient sample, medical device being used by the patient, caregiver name, caregiver photograph, caregiver ID, caregiver employer, a pharmacy record, pharmacy administration instructions, physicians orders.

5. A medication delivery apparatus as in claim 1, wherein tubing between the fluid conduit and a parenteral access device is 10 cm or less.

6. A medication delivery apparatus as in claim 1, further comprising: a transmitter within the housing to transmit information generated by the at least one sensor to the remote data collection system; and a self-contained power source within the housing powering the at least one first sensor and the transmitter.

7. A medication delivery apparatus as in claim 6, wherein the remote data collection system receives information wirelessly from the transmitter.

8. A medication delivery apparatus as in claim 1, wherein the housing comprises a reusable sub-housing and a disposable sub-housing, the disposable sub-housing being used by a single patient and including at least the fluid conduit and the medication port, the reusable sub-housing being used by a plurality of patients and including the at least one first sensor.

9. A medication delivery apparatus as in claim 8, wherein the re-usable sub-housing is operatively coupled to the disposable sub-housing by a connection interface including one or more of an electrical contact, an RF coupling, an optical coupling, a hydraulic coupling, a mechanical coupling, and a magnetic coupling.

10. A medication delivery apparatus as in claim 1, wherein the fluid conduit includes a first fluid channel and a second fluid channel, the first fluid channel extending from a first end to a second end, the second fluid channel extending from a distal end and terminating at the first fluid channel at an intersection intermediate the first end and the second end.

11. A medication delivery apparatus as in claim 1, wherein the medication delivery apparatus is integral to and/or configured to be suspended below a fluid source.

12. A medication delivery apparatus as in claim 1, wherein the information source is disposed proximate to a fitting of the tubing set.

13. A medication delivery apparatus as in claim 12, wherein the information source is disposed upon a cylindrical or annular surface that is concentric to the fluid outlet of the tubing set and the sensor generates the information characterizing administration of the medication when the tubing set is coupled and/or being coupled to the medication port.

14. A medication delivery apparatus as in claim 1, wherein the at least one first sensor includes a fluid flow sensor and wherein the information includes information indicative of an amount of fluid delivered from the medication source to the patient.

15. A medication delivery apparatus as in claim 1, wherein the at least one first sensor includes a medication composition type sensor, and wherein the information includes information characterizing the composition of the medication.

16. A medication delivery apparatus as in claim 1, wherein the remote data collection system receives, transmits, integrates and/or reports information from and/or to a medical information source selected from a group comprising: a medical device, and a medical information system.

17. A medication delivery apparatus as in claim 1, wherein the remote data collection system provides real-time information to a user including medication information, medical data specific to a patient, procedural instructions and/or protocols for patient treatment.

18. A medication delivery apparatus as in claim 1, wherein the remote data collection system provides a rule set defining conditions to alert and/or guide a caregiver using the apparatus.

19. A medication delivery apparatus as in claim 1, further comprising: a memory element disposed within the housing for storing information generated by the at least one first sensor.

20. A medication delivery apparatus as claim 1, further comprising: an indicator element disposed within the housing for indicating the operational state of the medication delivery apparatus and/or illuminating the medication port providing user information.

21. A medication delivery apparatus as in claim 1, wherein the at least one first sensor is selected from a group consisting of: a flow volume sensor, a flow rate measurement sensor, a composition sensor, a pressure sensor, an air in line sensor, and a temperature sensor.

22. A kit comprising a sterile pouch enveloping a medication delivery apparatus as in claim 1, wherein the medication delivery apparatus is provided within the pouch in a sterile condition.

23. A medication delivery apparatus for use with a medication source comprising:
   a housing;
   a fluid conduit at least partially extending within the housing and configured to deliver medication within the medication source to a patient;
   a medication port extending from an external surface of the housing and configured to be coupled to a fluid outlet of a tubing set coupled to the medication source, the medication port being fluidically and directly coupled to the fluid conduit, wherein the medication source is contained within a manually administratable medication container and the medication port has a shape and size to couple to the medication container;
   at least one sensor disposed within the housing to generate information characterizing administration of the medication;
   a transmitter within the housing to wirelessly transmit information generated by the sensor to a remote data collection system; and
   a self-contained power source within the housing powering the at least one sensor and the transmitter.

* * * * *